United States Patent
Kato et al.

(10) Patent No.: US 10,591,469 B2
(45) Date of Patent: Mar. 17, 2020

(54) IMMUNOASSAY METHOD AND IMMUNOCHROMATOGRAPHIC KIT

(71) Applicant: TANAKA KIKINZOKU KOGYO K.K., Chiyoda-ku, Tokyo (JP)

(72) Inventors: Yuya Kato, Hiratsuka (JP); Hisahiko Iwamoto, Hiratsuka (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 15/744,501

(22) PCT Filed: Jul. 15, 2016

(86) PCT No.: PCT/JP2016/071078
§ 371 (c)(1),
(2) Date: Jan. 12, 2018

(87) PCT Pub. No.: WO2017/010574
PCT Pub. Date: Jan. 19, 2017

(65) Prior Publication Data
US 2018/0209970 A1 Jul. 26, 2018

(30) Foreign Application Priority Data
Jul. 16, 2015 (JP) ................... 2015-141968

(51) Int. Cl.
| G01N 33/543 | (2006.01) |
|---|---|
| G01N 33/569 | (2006.01) |
| G01N 33/53 | (2006.01) |
| C12M 1/34 | (2006.01) |
| C12Q 1/04 | (2006.01) |

(52) U.S. Cl.
CPC ............ *G01N 33/543* (2013.01); *C12M 1/34* (2013.01); *C12Q 1/04* (2013.01); *G01N 33/53* (2013.01); *G01N 33/569* (2013.01); *G01N 33/56911* (2013.01); *G01N 33/56983* (2013.01)

(58) Field of Classification Search
CPC ........... G01N 2469/10; G01N 2400/00; G01N 2400/10; G01N 2400/18
See application file for complete search history.

(56) References Cited

U.S. PATENT DOCUMENTS

| 2008/0206849 A1* | 8/2008 | Zak ................. G01N 33/558 435/287.2 |
|---|---|---|
| 2013/0137192 A1 | 5/2013 | Iwamoto et al. |
| 2016/0370368 A1 | 12/2016 | Kato et al. |
| 2018/0021771 A1 | 1/2018 | Tamir |

FOREIGN PATENT DOCUMENTS

| CN | 103052884 A | 4/2013 |
|---|---|---|
| CN | 107530700 A | 1/2018 |
| EP | 0280557 A2 | 8/1988 |
| JP | H06-019353 B2 | 3/1994 |
| JP | H07-503543 B2 | 4/1995 |
| JP | 2002-202302 A | 7/2002 |
| JP | 2006-518990 A | 8/2006 |
| JP | 2007-178142 A | 7/2007 |
| JP | 2007-212343 A | 8/2007 |
| JP | 2007-315883 A | 12/2007 |
| JP | 2008-509384 A | 3/2008 |
| JP | 2009-036781 A | 2/2009 |
| JP | 2009-216695 A | 9/2009 |
| JP | 2011-099789 A | 5/2011 |
| JP | 2012-251789 A | 12/2012 |
| JP | 2014-232064 A | 12/2014 |
| JP | 2015-034719 A | 2/2015 |
| WO | WO 87/01393 A1 | 3/1987 |
| WO | WO 2005/121794 A1 | 12/2005 |
| WO | WO 2013/183621 A1 | 12/2013 |
| WO | WO 2015-020210 A1 | 2/2015 |
| WO | WO 2016/132223 A1 | 8/2016 |

OTHER PUBLICATIONS

EPO, Extended Search Report for EP application No. 16824554.6, dated Mar. 14, 2018.
PCT, International Search Report for PCT/JP2016/071078, dated Sep. 27, 2016.
CN, Office Action for Chinese application No. 201680041878.7, dated Feb. 2, 2019.
Xiao, et al., Chemical Research and Application, vol. 7, No. 4, pp. 378-381, Dec. 1995.
EP, Office Action for European application No. 16824554.6, dated Jun. 3, 2019.

* cited by examiner

*Primary Examiner* — Shafiqul Haq
(74) *Attorney, Agent, or Firm* — Orrick, Herrington & Sutcliffe LLP; Joseph A. Calvaruso; K. Patrick Herman

(57) ABSTRACT

The present invention is intended to provide an immunoassay method that enables an immunoassay with high sensitivity at a high development rate without causing aggregation of insoluble carriers or non-specific reaction while improving test efficiency and reducing labor. The present invention relates to an immunoassay method that uses a test device, and the method includes: extracting an antigen of a detection target in an analyte with an extraction agent; and detecting the detection target with a detection reagent capable of binding the antigen. The extraction agent is a nitrous acid generated on the test device by a contact reaction between a nitrite salt and a heterocyclic compound having at least one skeleton selected from the group consisting of a cyclic ester, a cyclic amide, and a cyclic imide.

14 Claims, 1 Drawing Sheet

[Fig.1A]
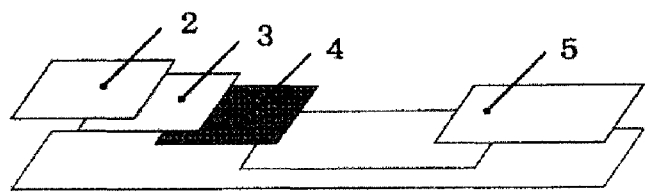
[Fig.1B]
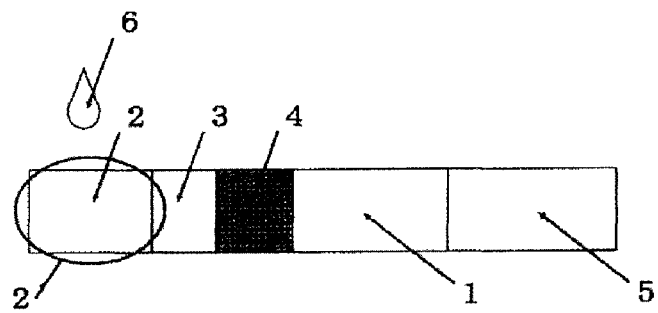

IMMUNOASSAY METHOD AND IMMUNOCHROMATOGRAPHIC KIT

TECHNICAL FIELD

The present invention relates to an easy-to-use, in vitro diagnostic kit, or an immunochromatographic kit that has values as a portable diagnostic device, for detecting a target substance (such as antigens) in a sample solution, for example, for the detection of gram-positive bacteria, particularly hemolytic streptococci, and for the simultaneous detection of gram-positive bacteria, particularly hemolytic streptococci, and viruses, particularly adenoviruses. The invention also relates to a reagent composition or an analyte processing solution, and a detection method for use in such kits. Particularly, the invention relates to a test method that uses a specific reagent composition for the preparation of a nitrous acid, which is essential for the extraction of polysaccharides in a *streptococcus* test, so that a nitrous acid can be generated with ease on a test device without having to separately prepare it fresh immediately before use, and the test efficiency and test accuracy improve.

BACKGROUND ART

An immunochromatographic strip immunoassay has become common as a convenient in vitro diagnostic kit or a portable diagnostic device for the detection of a target substance (such as antigens) in a sample solution using the specific reactivity of antibodies.

Lately, a convenient immunochromatographic testing tool that detects the presence or absence of an infection caused by pathogens such as influenza viruses and bacteria has attracted interest, and there has been ongoing research and development of such tools.

Hemolytic *streptococcus* (hereinafter, also referred to as "*streptococcus*") infections are diagnosed by a test that uses group-specific polysaccharides as antigens. Known methods of polysaccharide extraction use, for example, enzymes, phages, hydrochloric acid, and hypochlorous acid. The extraction method that uses nitrous acid is most common.

The extraction method using nitrous acid has a number of merits, including high extraction efficiency for polysaccharides, and the low price and the easy handling of nitrous acid. A drawback, however, is that the nitrous acid itself is an unstable, easily decomposable compound, and needs to be prepared fresh by mixing sodium nitrite and an organic acid such as acetic acid before extraction.

Such preparation of nitrous acid in each case is highly laborious for physicians and laboratory technicians when diagnosis is made on a regular basis. Further, because the process involves a mixing step, there is a possibility that the method may produce an inaccurate and unsafe diagnosis due to errors in mixing reagents. Another drawback is the poor assay repeatability due to the extraction time.

In order to overcome these drawbacks, there has been research and development of convenient testing tools that will simplify the extraction of polysaccharide antigens from hemolytic streptococci.

For example, patent document 1 proposes a simplified extraction method for the extraction of polysaccharide antigens from an organism (particularly, group A or B *streptococcus*) using a kit that combines a) a first absorbent material that is dried after being impregnated with a premeasured amount of a nitrite salt, b) a second absorbent material that is dried after being impregnated with a premeasured amount of a neutralizing base and a buffer, and c) a premeasured amount of an aqueous solution of an acid (see patent document 1).

A diagnosis of *streptococcus* infection is also a laborious process that requires first extracting a polysaccharide antigen, and then detecting the antigen by contacting the resultant solution with an immunoassay device. This has created a need for developing a method or a kit that allows for assaying an organism in a sample with ease with the step of extracting a polysaccharide antigen, and the step of measuring a marker.

For example, patent document 2 discloses a device and method for the detection of carbohydrate antigens that are characteristic of microbial/bacterial organisms, such as the family Streptococcacae. The lateral flow assay device provided in this publication includes a substrate having a) a sample receiving zone, b) an extraction zone (extraction reagent; an acid and a nitrite salt that are immobilized or absorbed and dried), c) neutralizing agent (neutralization buffer; TRIS), and d) a detection zone (capture/detection reagent) (see patent document 2).

A method and a kit for simultaneously assaying a plurality of organisms including streptococci are also developed. For example, patent document 3 describes a method and a kit for the measurement of a plurality of different biological species in a sample in which a first organism is a gram-positive bacterium, for example, a group A, B, F, or G *streptococcus*, and enterococcus bacteria, and a second organism is a virus, or a gram-negative bacterium.

The invention disclosed in patent document 3 is intended to enable a simultaneous detection of more than one analyte using a kit that includes, in one or more containers, a) nitrous acid, or an acid or a nitrite salt in a dry form, b) a surfactant, c) a first binding reagent that binds a first marker from a first organism, and d) a second binding reagent that binds a second marker from a second organism. This enables doubling the test efficiency, and relieves the pain caused in a patient by the test. The method also allows therapeutic agents that are effective against a plurality of causal organism types to be administered in an appropriate combination.

The nitrite salt is combined with acids such as inorganic acids (e.g., hydrochloric acid, sulfuric acid), and organic acids (acetic acid, citric acid). The preferred acids are organic acids, more preferably acetic acid. Acetic acid is used in Examples (see patent document 3).

A *streptococcus* test typically uses group-specific polysaccharide antigens because *Streptococcus* have many serotypes. The extraction method using nitrous acid is a known method of extraction of polysaccharides from bacteria. However, being an unstable compound, nitrous acid needs to be prepared fresh by mixing sodium nitrite and an organic acid immediately before use.

This is problematic because the nitrous acid preparation adds to the test steps, and involves poor assay repeatability due to variation in the preparation technique, and the extraction time. The present inventors have successfully simplified the procedures, and improved the assay repeatability with an immunochromatographic kit having two sample pads separately impregnated with sodium nitrite and citric acid. A problem, however, is the poor extraction efficiency due to the non-specific color produced when an increased amount of citric acid is impregnated.

A *streptococcus* infection is a respiratory infection that is common year round, and *Streptococcus* species represent a group of known causative microorganisms of common cold in Europe and the United States, in addition to Japan. Easy and quick immunochromatographic diagnosis kits are used to assist diagnosis. (About 3 million tests are conducted per year in the market.)

Assay devices and methods for the detection of carbohydrate antigens that are characteristics of microbial/bacterial organisms such as the family Streptococcacae are already commercially available in the market. Known examples of currently available immunochromatography reagents include the QuickVue DipStick Strep A (DS Pharma Biomedical), and the StrepA Test Pack—Plus OBC (Sanwa Kagaku Kenkusho). Slide latex agglutination reagents, for example, the A Strept AD "Seiken" (Denka Seiken), are also known.

In commercially available immunochromatography reagents, a *streptococcus* concentration of at least $1 \times 10^6$ CFU/mL is typically required for the direct method, in order to produce a positive test result in testing an analyte. This is problematic because, when the *streptococcus* concentration is less than $1 \times 10^6$ CFU/mL, an analyte that should produce a positive test result will be tested negative. Another problem is that an immunochromatographic test agent with a labeled antibody conjugated to an insoluble carrier typically has lower sensitivity than EIA, and produces an unclear line for a positive test result. Further, the traditional reagents involve a false positive, which wrongly indicates a positive result despite the absence of a target substance (such as antigens) in a sample solution.

In order to solve these problems, methods are proposed that mix a sugar or a water-soluble polymer compound into a development solvent. For example, a membrane assay using antibody-conjugated colored latex particles is proposed that uses an immunoassay latex composition containing at least one aggregation preventing agent such as sugar group, for example, such as monosaccharides, oligosaccharides, and sugar alcohols and polyalcohols thereof in a latex composition, and a basic buffer with an added protein, and having a pH of 9.0 to 9.8. In this way, the method prevents natural aggregation of latex particles, and increase of specific gravity, viscosity, and osmotic pressure to enable a high-sensitive immunoassay (see patent document 4).

Glycohemoglobin (blood hemoglobin with sugar attached to it), particularly hemoglobin A1c (referred to as "HbA1c") with the glycated valine residue at the N-terminal of the hemoglobin β chain is widely used as an index suited for the diagnosis of diabetes. With regard to a particle immunochromatography assay of these hemoglobins, a detection method is recently proposed that includes (A) treating a red blood cell-containing measurement sample with a surfactant to expose the N terminal of the hemoglobin β chain to protein surface, (B) contacting the resultant sample to a water-insoluble state of cyclic polysaccharides (for example, the cyclic polysaccharides are immobilized on membrane or the like by chemical bonding, and form a polymer by themselves in a state of being kneaded into a porous resin), and (C) contacting the sample to antibodies or the like that recognize the N terminal of the particle-labeled hemoglobin.

In this way, the method prevents the constituent cyclic oligosaccharide or polysaccharide molecules of cyclic polysaccharides from dissolving in water and becoming non-diffusive upon contact between cyclic polysaccharides and water, which is a cause of inaccurate measurement due to the antibodies forming aggregates, and failing to develop on a membrane (see patent document 5).

With regard to the simplified analyte test method based on membrane assay, an analyte sample filtration method is proposed that can prevent a false positive or clogging while maintaining sensitivity (see patent document 6).

However, with the immunochromatography method (also referred to as "particle immunochromatography method") using antibodies conjugated to an insoluble carrier (metal particles, colored latex particles, etc.), aggregation of the insoluble carrier still occurs depending on the measurement sample, measurement environment, and measurement conditions. This may cause non-specific reactions, and the slow development rate remains a problem. There accordingly is a strong need for the pursuit of a test agent that does not cause aggregation of insoluble carriers, or non-specific reactions, and therefore has a fast development rate in a particle immunochromatography method performed with different measurement samples under different measurement environments or conditions.

RELATED ART

Patent Document

Patent document 1: JP-T-H7-503543
Patent document 2: JP-T-2008-509384
Patent document 3: JP-T-2006-518990 (Japanese Patent No. 4667874)
Patent document 4: JP-A-2007-315883
Patent document 5: JP-A-2012-251789
Patent document 6: JP-A-2009-36781

DISCLOSURE OF INVENTION

Technical Problem

It is an object of the present invention to provide an immunoassay method, an immunochromatographic detection method, and an immunochromatographic kit (also referred to as "immunochromatography kit") for testing of, for example, gram-positive bacteria, particularly streptococci, whereby the unstable compound nitrous acid is generated on a test device for the extraction of polysaccharides contained in the cell wall on the surface of a *streptococcus* cell to improve test efficiency and reduce labor, and to enable a highly sensitive immunoassay at a high development rate, without causing aggregation of insoluble carriers, and non-specific reactions.

By modifying an analyte diluting solution (also referred to as "analyte processing solution" or "developer"), the invention enabled reducing a color signal from a negative analyte, and enhancing a color signal from a positive analyte in the development system, as compared to the related art. Specifically, the invention has enabled providing a high-sensitive test agent for immunochromatography by improving the test accuracy (hereinafter, also referred to as "S/N ratio") through a contact reaction of a specific heterocyclic compound and a nitrite salt.

The present invention is also intended to provide a test agent for immunochromatography that, with the modified extraction agent, enables immunochromatographic testing of bacteria, or both bacteria and viruses at the same time, with high sensitivity and at a high development rate, without causing the protein component in an analyte or in a test device to denature or precipitate during the development in the test.

It is yet another object of the present invention to provide an immunoassay reagent, an immunoassay method, an immunochromatographic detection method, and an immunochromatographic kit that, with the improved configuration of the attachment site of an immunochromatographic kit, enable extraction of microorganisms, or antigens or antibodies derived from microorganisms (for example, gram-positive bacteria, particularly hemolytic streptococci) in a sample (for example, an analyte collected from respiratory disease patients, specifically a pharyngeal swab, saliva, a nasal discharge, a nasal swab, or phlegm, etc.) at a faster rate and with higher accuracy than in the related art, with the use of the nitrous acid generated on a test device, and thereby improve test efficiency and accuracy, and reduce labor in immunochromatographic testing of bacteria, or both bacteria and viruses at the same time.

More specifically, the present invention is intended to provide a sample extractant (hereinafter, also referred to as "sample diluting solution") and a reagent for immunochromatography that are easy to use and having high sensitivity with a high S/N ratio, and that enable a quick diagnosis through detection of a group A β-hemolytic *streptococcus*, which causes respiratory infections, or simultaneous detection of group A β-hemolytic *streptococcus* and adenovirus. The present invention is also intended to provide an immunochromatographic kit, and a test method using the extractant and the reagent.

Solution to Problem

The present inventors impregnated a nitrite salt, and a heterocyclic compound having at least one of the skeletons selected from the group consisting of a cyclic ester, a cyclic amide, and a cyclic imide in a test device, and has made it possible, for the first time, to provide an immunoassay method and an immunochromatographic kit that are easy to use and having high detection sensitivity and specificity.

In order to enable immunochroamtographic testing of bacteria, or both bacteria and viruses at the same time, the present inventors contained a nitrite salt in the analyte diluting solution used, or in a reagent retaining section positioned upstream of another reagent retaining section retaining a heterocyclic compound having at least one skeleton selected from the group consisting of a cyclic ester, a cyclic amide, and a cyclic imide in the direction of sample development.

Denaturated or precipitated protein component in the analyte or in the test device does not becomes captured in the detection section, if pH condition of the developer which is the analyte diluting solution is varied due to generated nitrous acid or coexisting organic compounds, various compounds that belong to the domain of the heterocyclic compound having any of the cyclic ester, cyclic amide, and cyclic imide skeletons retained in the test device. Therefore, a test agent having a fast development rate with high test accuracy (S/N ratio) that does not cause aggregation of antibody-immobilized metal particles or induce a non-specific reaction depending on the above situation is realized.

A detection system of the present invention provides an immunoassay reagent, an immunoassay method, and an immunochromatographic kit that enable testing without causing the protein or other components in the extractant or analyte, or in a test device to precipitate even when a heterocyclic compound having at least one skeleton selected from the group consisting of a cyclic ester, a cyclic amide, and a cyclic imide is present as a reagent component in the test performed with the presence of a cyclic oligosaccharide, or under the development/extraction conditions that generate nitrous acid.

The present invention has been completed with the specific means by which the foregoing problems can be solved, specifically, the analyte processing solution, the immunoassay reagent, the immunoassay method, the immunochromatographic detection method, and the immunochromatographic kit for immunochromatography method, and the immunochromatography method using same, as recited in the items (1) to (19) below.

An immunoassay method of the present invention has the following features.

(1) The first feature of the present invention is an immunoassay method that uses a test device, the method comprising: extracting an antigen of a detection target in an analyte with an extraction agent; and detecting the detection target with a detection reagent capable of binding the antigen, wherein the extraction agent is a nitrous acid generated on the test device by a contact reaction between a nitrite salt and a heterocyclic compound having at least one skeleton selected from the group consisting of a cyclic ester, a cyclic amide, and a cyclic imide.

(2) The second feature of the present invention is the immunoassay method, wherein the heterocyclic compound having a cyclic ester skeleton is a five-membered ring compound having 1 to 2 oxygen atoms.

(3) The third feature of the present invention is the immunoassay method, wherein the heterocyclic compound having a cyclic amide skeleton, and the heterocyclic compound having a cyclic imide skeleton are five- or six-membered ring compounds having 1 to 3 nitrogen atoms.

(4) The forth feature of the present invention is the immunoassay method, wherein the heterocyclic compound having at least one skeleton selected from the group consisting of a cyclic ester, a cyclic amide, and a cyclic imide is used in an amount of 0.1 to 100 μmol per measurement.

(5) The fifth feature of the present invention is the immunoassay method, wherein the detection reagent contains an antibody derived from at least one animal species selected from rabbit, goat, and mouse.

(6) The sixth feature of the present invention is the immunoassay method, wherein an assay is conducted in the presence of a cyclic oligosaccharide.

(7) The seventh feature of the present invention is the immunoassay method, wherein the antigen is a polysaccharide.

(8) The eighth feature of the present invention is the immunoassay method, wherein the detection target is a gram-positive bacterium.

(9) The ninth feature of the present invention is the immunoassay method, wherein the detection target is a gram-positive bacterium and an adenovirus.

(10) The tenth feature of the present invention is the immunoassay method, wherein the gram-positive bacterium is a hemolytic *streptococcus*.

An immunochromatographic kit of the present invention has the following features.

(11) The eleventh feature of the present invention is an immunochromatographic kit for detecting an antigen of a detection target in an analyte with a detection reagent capable of binding the antigen, the immunochromatographic kit comprising: an analyte diluting solution; and an immunochromatographic device that includes: a sample dropping section; an antigen extracting section; a label-substance retaining section; a chromatographic medium having a detection section; and an absorbing section, wherein at least one of the analyte diluting solution and the sample dropping section contains a nitrite salt, and wherein the antigen extracting section contains a heterocyclic compound having at least one skeleton selected from the group consisting of a cyclic ester, a cyclic amide, and a cyclic imide.

(12) The twelfth feature of the present invention is the immunochromatographic kit, wherein the heterocyclic compound having at least one skeleton selected from the group consisting of a cyclic ester, a cyclic amide, and a cyclic imide is contained in an amount of 0.1 to 100 μmol per kit.
(13) The thirteenth feature of the present invention is the immunochromatographic kit, wherein the detection reagent contains an antibody derived from at least one animal species selected from rabbit, goat, and mouse.
(14) The fourteenth feature of the present invention is the immunochromatographic kit, wherein at least one of the analyte diluting solution and the sample dropping section contains a cyclic oligosaccharide.
(15) The fifteenth feature of the present invention is the immunochromatographic kit, wherein the antigen is a polysaccharide.
(16) The sixteenth feature of the present invention is the immunochromatographic kit, wherein the detection target is a gram-positive bacterium.
(17) The seventeenth feature of the present invention is the immunochromatographic kit, wherein the detection target is a gram-positive bacterium and an adenovirus.
(18) The eighteenth feature of the present invention is the immunochromatographic kit, wherein the gram-positive bacterium is a hemolytic *streptococcus*.
(19) The nineteenth feature of the present invention is the immunochromatographic kit, which uses a metal nanoparticle carrier as a label component for use in the label-substance retaining section.

The present invention can solve the problem by providing the above features.

Effects of the Invention

The present invention extracts the group-specific polysaccharides that are present in the cell wall on the surface of gram-positive bacteria, particularly streptococci (groups A to V), by using the nitrous acid that generates when a premeasured amount of a nitrite compound is mixed and contacted with a premeasured amount of a heterocyclic compound having at least one skeleton selected from the group consisting of a cyclic ester, a cyclic amide, and a cyclic imide, and uses the polysaccharides as antigens in a test. The invention can thus provide an easy and versatile test kit and method that do not involve an error as might occur when mixing reagents, or do not require the need to separately prepare nitrous acid fresh immediately before use.

Specifically, nitrous acid can be generated on a test device without the laborious nitrous acid generating process of reacting a nitrite salt with an acidic solution for every test. This has made it possible to omit the complication of the test and provide a simplified test method having improved test efficiency and accuracy.

A *streptococcus* detection system using the immunochromatographic kit of the present invention uses a heterocyclic compound having at least one skeleton selected from the group consisting of a cyclic ester, a cyclic amide, and a cyclic imide. In this way, a test can be quickly performed with high sensitivity without causing the protein component in the extractant or in the analyte to precipitate during the extraction/development.

Specifically, by using a sample extractant (also referred to as "analyte diluting solution") for immunochromatography containing a heterocyclic compound having at least one skeleton selected from the group consisting of a cyclic ester, a cyclic amide, and a cyclic imide, the present invention has enabled providing a test agent that enables an accurate detection with a fast development rate without causing protein precipitation during the development, or aggregation of antibody-immobilized metal particles.

Further, by using the nitrous acid that generates when a premeasured amount of a nitrite compound is mixed and contacted with a premeasured amount of a heterocyclic compound having at least one skeleton selected from the group consisting of a cyclic ester, a cyclic amide, and a cyclic imide, the present invention has enabled providing a kit that enables extraction of the group-specific polysaccharides present in the cell wall on the surface of the gram-positive bacteria, particularly streptococci (groups A to V), and extraction of the protein present in adenovirus, and simultaneous testing of the antigens from each of the gram-positive bacteria and the adenovirus (or simply "Adv") with a label conjugated to the corresponding antibodies immobilized on test lines.

Further, by containing a cyclic oligosaccharide in a reagent retaining section [2], the present invention offers an advantage that the result can be determined both quickly and conveniently with high sensitivity, without denaturing or precipitating the antigens (for example, gram-positive bacteria, particularly streptococci, and viruses) in a sample analyte (specifically, a pharyngeal swab, saliva, a nasal discharge, a nasal swab, phlegm, etc.) collected from, for example, a respiratory disease patient, even when an organic compound, specifically, a heterocyclic compound having at least one skeleton selected from the group consisting of a cyclic ester, a cyclic amide, and a cyclic imide is retained in the reagent retaining section, or under the conditions that generate nitrous acid.

BRIEF DESCRIPTION OF DRAWINGS

FIG. 1A and FIG. 1B are diagrams showing an immunochromatographic device of the present invention, in which FIG. 1A shows a spatial perspective view of the immunochromatographic device, and FIG. 1B shows a plan view of the immunochromatographic device.

EMBODIMENTS FOR CARRYING OUT THE INVENTION

The present invention is described below in detail.

An embodiment of the present invention is based on an immunoassay method or a detection method using same in which the antigen of a detection target material of interest for detection in an analyte is conjugated by antigen-antibody reaction with a labeled detection reagent (antibody) capable of binding the antigen, and in which the conjugate is confirmed by various means of detection. Antibodies that react and bind to the antigen with the highest specificity may be selected from any known antibodies, including, for example, monoclonal antibodies and polyclonal antibodies, that specifically bind to the antigen.

The following descriptions of the immunoassay method of the present invention are based in part on an immunochromatography method using a chromatographic medium. However, the present invention is not limited to the immunochromatography method.

The label may be any label, including, for example, enzymes, chromogenic substances, fluorescent substances, and radioactive substances, and may be decided to take advantage of the characteristics of the immunochromatography method, which include, for example, ease of operation, and a short assay time, or may be decided in consideration of the type of antibody or antigen.

The detection means is characterized by its ability to make accurate determination by visual inspection, so that the characteristics of the immunochromatography method, for example, ease of operation, and a relatively short time needed to make determination, can be exploited. However, when factors such as time and accuracy are of concern, detection may be made by using additional detection means, for example, such as spectrophotometric detection, and radiation detection.

The following describes the best form of the analyte diluting solution (also referred to as "analyte processing solution"), the immunoassay reagent, the immunoassay method, the immunochromatographic detection method, and the immunochromatographic kit that can be used for the immunoassay method of the present invention, in order.

The immunoassay reagent of the present invention is a reagent for an immunoassay, and is used by being contained in an analyte diluting solution (also referred to as "analyte processing solution", or "analyte extractant"), and/or by being contained and retained in a sample dropping section [2] (also referred to as "reagent retaining section [2]"). Additionally, the immunoassay reagent may also be contained and retained in at least one of a reagent retaining section [3] (also referred to as "antigen extracting section" [3]), a label-substance retaining section [4], and a chromatographic medium [1]. The property of the reagent is such that, when contained in the analyte diluting solution or in the sample dropping section [2], the reagent moves and develops from the reagent retaining section [3] (antigen extracting section) to the label-substance retaining section [4], and to the chromatographic medium [1] and the absorbing section [5].

The immunoassay reagent of the present invention may be a nitrite compound contained in at least one of the analyte diluting solution and the reagent retaining section [2], either independently or at the same time. The immunoassay reagent of the present invention may be a nitrite compound and a cyclic oligosaccharide contained in at least one of the analyte diluting solution and the reagent retaining section [2], either alone or at the same time. This may be implemented, for example, as follows.

The following represents examples of specific implementations concerning the components containing a nitrite compound (or "NR" for short), and a cyclic oligosaccharide (or "CO" for short), and the sites containing these components in the present invention. The examples below represent the implementations (patterns) in which NR, and NR and/or CO are contained in the analyte diluting solution (analyte processing solution) [6], and the sample dropping section [2] (reagent retaining section [2]).

| Pattern | Analyte diluting solution (analyte processing solution) [6] | Sample dropping section [2] |
|---|---|---|
| 1 | NR | None |
| 2 | None | NR |
| 3 | NR | NR |
| 4 | None | NR and CO |
| 5 | NR | CO |
| 6 | CO | NR |
| 7 | NR and CO | None |
| 8 | NR and CO | NR and CO |
| 9 | NR and CO | NR |
| 10 | NR | NR and CO |
| 11 | CO | NR and CO |
| 12 | NR and CO | CO |

The present invention may be carried out in the foregoing implementations (patterns).

The state of the reagent in the sample dropping section [2] (reagent retaining section [2]) include a solution form, and a retained form in a dropping pad such as by freeze drying.

The heterocyclic compound having at least one skeleton selected from the group consisting of a cyclic ester, a cyclic amide, and a cyclic imide used in the present invention is described below. The heterocyclic compound is used in an amount typically in a range of 0.05 to 100 µmol, preferably 0.1 to 100 µmol, more preferably 0.1 to 50 µmol, further preferably 0.1 to 30 µmol, optimally 1 to 15 µmol per measurement (per kit).

In order to efficiently generate nitrous acid, it would be reasonable to add the heterocyclic compound having at least one skeleton selected from the group consisting of a cyclic ester, a cyclic amide, and a cyclic imide in catalytic amounts to small amounts with respect to the nitrite salt. However, the amount of nitrite salt may be freely adjusted in a range of typically 1 µmol to 500 µmol, preferably 5 to 200 µmol, more preferably 10 to 100 µmol for 0.05 to 100 µmol of the heterocyclic compound, taking into consideration generation of the nitrous acid, or according to the type of the salt component of the nitrous acid.

Specifically, nitrous acid in a free acid form induces a self oxidation-reduction reaction as the concentration increases, and is typically used in low concentrations, or produced by making a nitrite salt acidic at low temperature. However, by using the heterocyclic compound having at least one skeleton selected from the group consisting of a cyclic ester, a cyclic amide, and a cyclic imide in catalytic amounts to small amounts as in the present invention, the reaction ideally proceeds in a milder and more uniform fashion even under ordinary temperature than when organic acids, for example, such as citric acid, and acetic acid are used, and a nitrous acid generates in a predetermined uniform concentration.

This should yield a favorable result by reducing nonspecific color production, providing dispersibility and stability for the metal particles, and thereby improving the S/N ratio, and making visual inspection easier. Using the heterocyclic compound in excess amounts, rather than catalytic amounts to small amounts, does not pose any problem. However, evidently, this is not cost effective as the heterocyclic compound will be wasted.

The specific mechanism as to how the heterocyclic compound having at least one skeleton selected from the group consisting of a cyclic ester, a cyclic amide, and a cyclic imide used in the present invention acts on nitrite salt remains unclear. Presumably, the heterocyclic compound has a catalytic role to accelerate the decomposition of the nitrite salt into a nitrous acid and a base, which occurs as the nitrite salt dissolves in water contained in the development extractant or in the analyte diluting solution.

In the present invention, the nitrite salt is not particularly limited, as long as it quickly generates nitrous acid upon contact with a specific organic compound, and does not cause adverse effects on the test device in a test. Examples of the nitrite salt include sodium nitrite, potassium nitrite, calcium nitrite, magnesium nitrite, silver nitrite, zinc nitrite, and mixtures of these. The nitrite salt is preferably an alkali metal salt of nitrous acid, most preferably sodium nitrite.

The nitrite salt content in the immunoassay reagent is 1 to 500 µmol/test, preferably 5 to 200 µmol/test, more preferably 10 to 100 µmol/test. Processed food may contain small amounts, typically about 0.5 to 4 µg/g of nitrous acid radicals ($NO^{2-}$), and the free acid form is unstable, and tends to decompose. The immunoassay method of the present invention is a system that allows testing in a short time period with the nitrous acid generated at the site of measurement, and can very effectively take advantage of the function of nitrous acid.

With a low nitrite salt content of less than 1 μmol/test, there will be only small generation of nitrous acid. Accordingly, the test accuracy (S/N ratio) is low, and a longer time will be needed to make determination, with the result that the test efficiency tends to decrease. With a high nitrite salt content of more than 500 μmol/test, the concentration of the nitrous acid itself increases, and the self oxidation-reduction reaction of nitrous acid, and the development rate become problems that need to be taken into consideration. After all, this is not desirable in terms of handling, S/N ratio, and test time.

The cyclic oligosaccharide used for the immunoassay reagent of the present invention, and that is used in at least one of the analyte diluting solution and the sample dropping section is contained in a content of typically 0 to 20 μmol preferably, 0.1 to 5 μmol more preferably 0.5 to 2 μmol/test per immunochromatographic kit.

The cyclic oligosaccharide does not pose any problem in a test even when absent. However, the S/N ratio tends to increase with the cyclic oligosaccharide. However, the recommended appropriate content is about 0.1 to 5 μmol because increasing the content to a relatively high content of more than 20 μmol/test does not usually produce a corresponding increase in S/N ratio.

The cyclic oligosaccharide used in the present invention is not particularly limited, as long as it is an oligosaccharide having a structure in which D-glucose and/or derivatives thereof are forming a cyclic structure by α (1→4) glycosidic linkage.

Specific examples of the cyclic oligosaccharide include cyclodextrins, for example, such as α-cyclodextrin, β-cyclodextrin, and γ-cyclodextrin; (α-, β-, or γ-) cyclodextrin derivatives, such as hydroxyalkylated cyclodextrin, sulfoalkylated cyclodextrin, monochlorotriazinyl cyclodextrin, cluster cyclodextrin, and modified cluster cyclodextrin; and cyclic glycans, such as cycloamyloses containing about 20 to 50 glucose units bound together in a ring, laurylated cycloamyloses, and water-soluble xylans—derivatives of cycloamyloses. These cyclodextrins and cyclic glucans may be used as a mixture.

Preferred are at least one selected from β-cyclodextrins, and γ-cyclodextrins (see JP-A-2012-188573, and JP-A-2012-251789).

Cyclic oligosaccharides have a specific cyclic structure, typically with an outer hydrophilic portion, and an inner hydrophobic (lipophilic) portion. Because of such a specific structure, cyclic oligosaccharides can form a complex by incorporating a lipophilic molecule of a size smaller than the inner diameter of the cyclic structure. It is also known that cyclic oligosaccharides also can form a complex by incorporating molecules larger than the inner diameter of the cyclic structure, provided that the molecules have a lipophilic portion smaller than the inner diameter of the cyclic structure.

In the present invention, a hydrocarbon functional group as a lipophilic moiety of an organic compound molecule is incorporated in the cyclic oligosaccharide, and formation of a conjugate between the organic compound and a protein component derived from the target material or other biological materials in a sample, or a protein component contained in additives or other materials in the immunochromatographic kit can be reduced. This makes it possible to prevent a low development rate or development errors caused by a non-specific reaction due to the conjugate formation, or precipitation of the conjugate.

The cyclic oligosaccharide present in the immunoassay reagent of the present invention is particularly preferably an α-cyclodextrin, a β-cyclodextrin, a γ-cyclodextrin, or a derivative of these.

Preferred for use as the analyte (test sample) in the present invention are samples containing gram-positive bacteria having a thick peptidoglycan layer. Examples of such bacteria include staphylococci, streptococci, pneumococci, *bacillus, Bacillus anthracia, Bacillus cereus, Corynebacterium diphtheriae, Listeria, Clostridium tetani, Clostridium botulinum*, and *Clostridium perfringens*. The immunochromatographic kit of the present invention is used preferably with a sample containing cocci, specifically staphylococci, streptococci, or pneumococci, most preferably streptococci.

Samples containing gram-positive bacteria are not particularly limited, and may be, for example, biological samples such as saliva, a nasal discharge, a nasal swab, a nasal aspirate, phlegm, a pharyngeal swab, an alveolar wash, rectal swab, a fecal suspension, urine, and amniotic fluid. Other examples include food extracts, clean water, sewage, and broths. The invention is useful when the causative bacteria contained in the analyte contain gram-positive bacteria, particularly streptococci. Specifically, the gram-positive bacteria used as a detection target in the immunochromatographic kit of the present invention are hemolytic streptococci. The detection system of the present invention using an extraction agent generated by the reaction of a nitrite salt and the heterocyclic compound having at least one skeleton selected from the group consisting of a cyclic ester, a cyclic amide, and a cyclic imide is applicable to any bacteria, provided that a bacteria-specific antigenic polysaccharide can be extracted with the generated extraction agent nitrous acid.

The test sample in the present invention is not limited to gram-positive bacteria, particularly streptococci, and a sample containing different microorganisms, such as viruses, also may be preferably used. Examples of viruses include adenoviruses, influenza viruses (A, B, or C), rhinoviruses, coronaviruses, herpesviruses, and papillomaviruses.

The present invention enables obtaining antigens (polysaccharide antigens, protein antigens) from the same sample (a nasal discharge, a pharyngeal swab, etc.) using the same extraction agent. This has made it possible to develop a test kit for conventionally difficult simultaneous testing of adenovirus and *streptococcus*.

The immunoassay method of the present invention can inhibit denaturation and precipitation of high-viscosity proteins contained in an analyte such as a nasal discharge, and denaturation and precipitation of proteins that are present in a test device, which are caused by the heterocyclic compound having at least one skeleton selected from the group consisting of a cyclic ester, a cyclic amide, and a cyclic imide, or by the nitrous acid generated in the detection system. There accordingly will be no decrease of development rate due to the clogging of pores in the chromatography material, and viscosity increase due to high-viscosity proteins or other materials can be inhibited. This enables high-speed development without deterioration of sensitivity, and a fast analyte detection is possible.

A feature of the immunoassay method is that the extraction agent (extraction reagent) is the nitrous acid that generates on a test device by the reaction of a nitrite salt with the heterocyclic compound having at least one skeleton selected from the group consisting of a cyclic ester, a cyclic amide, and a cyclic imide, specifically in the organic compound-containing antigen extracting section (reagent retaining section [3]). Preferably, the immunoassay method is carried out with a non-ionic surfactant (described below) retained with the heterocyclic compound having at least one skeleton selected from the group consisting of a cyclic ester, a cyclic amide, and a cyclic imide.

The extraction agent (extraction reagent), or the nitrous acid generated by the contact reaction between a nitrite salt and the heterocyclic compound having at least one skeleton selected from the group consisting of a cyclic ester, a cyclic amide, and a cyclic imide has an extracting pH of preferably 6.8 to 7, for the reasons described below.

*Streptococcus* detection by the immunochromatography method typically uses the group-specific polysaccharides on bacteria surface as antigens. In antigen extraction, nitrous acid allows for extraction with much higher efficiency than extractants containing various enzymes. However, problems occur when the pH becomes acidic during the development because of the acid contained in the reagent retaining section, or the generated nitrous acid. Specifically, precipitation of the proteins, for example, casein, or a salt thereof present in the immunochromatographic detection system, or precipitation of high-viscosity proteins contained in the analyte becomes a problem.

By using a common extractant of a form containing 1) an enzyme, 2) an added salt, 3) a surfactant, 4) an ionic liquid, 5) a (nitrous acid generating) catalyst, and 6) nitrous acid, the present inventors conducted multidimensional studies by focusing on the behavior of the 1) enzyme. As expected, in an extractant system containing 1) to 5), the antigen extraction efficiency was found to be lower than in a system containing 6) nitrous acid. While the result showed that nitrous acid was indeed necessary for antigen extraction, nitrous acid generates under acidic conditions, and it is very difficult to use nitrous acid with the common extractant because the protein casein in the common extractant precipitates under acidic conditions. The present invention therefore conducted a search for acidic conditions under which nitrous acid can be generated without causing precipitation of casein.

[Behavior of a System Using Common Extractant and Nitrous Acid]

| pH | 6 | 6.5 | 6.8 | 7 | 8 |
|---|---|---|---|---|---|
| Bubbles (nitrous acid) | Present | Present | Slightly present | Absent | Absent |
| Precipitation (casein) | Present | Slightly present | Absent | Absent | Absent |

From the result of analysis, it was found that nitrous acid can be used with the common extractant under the pH condition of about 6.5 to 7. In order to achieve improved antigen extraction efficiency, the present invention conducted an investigation from two different approaches: common extractant and kit configuration, as follows.

After further investigations and studies of the foregoing problem, the pH condition that allows for generation of nitrous acid without causing precipitation of proteins such as casein, or precipitation of high-viscosity proteins contained in the analyte was found to be a pH of less than 7.0 to 6.5, preferably less than 7.0 to 6.6, most preferably less than 7.0 to 6.8 in the present invention.

With a pH of 7 or more, only small amounts of nitrous acid generate, and detection sensitivity is poor because of low antigen extraction efficiency. The antigen extraction efficiency by the generated nitrous acid improves under an acidic condition with a pH of less than 6.5. However, precipitation of proteins such as casein, and precipitation of high-viscosity proteins contained in the analyte occur under such acidic conditions, and prevent detection.

The immunochromatographic kit of the present invention is designed to develop an analyte under neutral to weakly acidic conditions for the generation of nitrous acid. The immunochromatographic kit is also designed to enable tests with existing extractants used for respiratory infections.

However, the components (casein) contained in the extractant precipitate under weakly acidic conditions, and development does not proceed uniformly. In order to solve this problem, the present inventors conducted studies to reduce precipitation of such components by adding various compounds. It was found as a result that precipitation of extractant components can be reduced, and the uniformity of development improves when a cyclic oligosaccharide is contained in the detection system, for example, in the nitrite salt-containing section or in the analyte diluting solution.

It was confirmed that the present invention can be properly implemented when nitrous acid is generated preferably under neutral to weakly acidic development conditions (pH=6.8). This design condition can also accommodate testing with existing extractants used for respiratory infections.

However, the components (casein) contained in the extractants precipitate under weakly acidic conditions, and development does not proceed uniformly. After the studies conducted to reduce precipitation of such components by adding various compounds, it was found that precipitation of extractant components can be reduced, and the uniformity of development improves by containing cyclodextrins (CD), particularly β-cyclodextrin (β-CD). The following shows the patterns found by the studies. Note here that BSA stands for bovine serum albumin, PEG stands for polyethylene glycol (PEG 20000), and TH stands for trehalose.

| | No addition | BSA | PEG | TH | β-CD |
|---|---|---|---|---|---|
| Uniformity of development | Slightly nonuniform | Non-uniform | Non-uniform | Slightly nonuniform | Uniform |

The same pattern can be confirmed for various other CDs representing cyclic oligosaccharides.

The antigen extractant used in the present invention, specifically, the extractant that serves as the sample extractant (analyte diluting solution) or development extractant may contain common components including a nitrite (e.g., a nitrite salt), a neutralizing base (e.g., sodium hydroxide), and a buffer (e.g., TRIS).

The extractant may also contain substances having the effect to inhibit side reactions due to biological affinity, or cancel hydrophobic bonding or electrical interaction, for example, such as surfactants, ammonium salts, sugars (e.g., cyclic oligosaccharides), and pH buffer. The extractant may also contain various additives for inhibiting non-specific reactions, for example, proteins or polymeric compounds for promoting antigen-antibody reaction or inhibiting non-specific reaction.

The behaviors of various compounds that belong to the domain of the cyclic oligosaccharide above, and the effects of these compounds on the developer have been tested by the analyses conducted by the present inventors (see JP-A-2015-034719).

The compound used for the extractant system may be a compound that generates nitrous acid upon contact with a nitrite compound, and that does not cause denaturation or precipitation of proteins or other materials present in the test device, specifically, a heterocyclic compound having at least one skeleton selected from the group consisting of a cyclic ester, a cyclic amide, and a cyclic imide.

Preferably, the compound is a five- or six-membered ring heterocyclic compound having at least one skeleton selected from the group consisting of a cyclic ester, a cyclic amide, and a cyclic imide, more preferably a five- or six-membered ring heterocyclic compound having at least one of the skeletons of a cyclic ester, and a cyclic imide.

Examples of the five- or six-membered ring heterocyclic compound having a cyclic ester skeleton include ascorbic acid (A1), erythorbic acid, dehydroacetic acid, ethylene carbonate, 2-O-(α-D-glucopyranosyl)-L-ascorbic acid, and 2,3,7,8-tetrahydroxy[1]benzopyrrano[5,4,3-cde][1]benzopyran-5,10-dione dihydrate (A3).

Most preferred are ascorbic acid, 2-O-(α-D-glucopyranosyl)-L-ascorbic acid (A2), and 2,3,7,8-tetrahydroxy[1]benzopyrrano[5,4,3-cde][1]benzopyran-5,10-dione dihydrate.

Preferably, the heterocyclic compound having a cyclic ester skeleton is a five-membered ring compound having 1 to 2 oxygen atoms.

The following chemical structures represent examples of the five- or six-membered ring heterocyclic compound having a cyclic ester skeleton.

[Chem. 1]

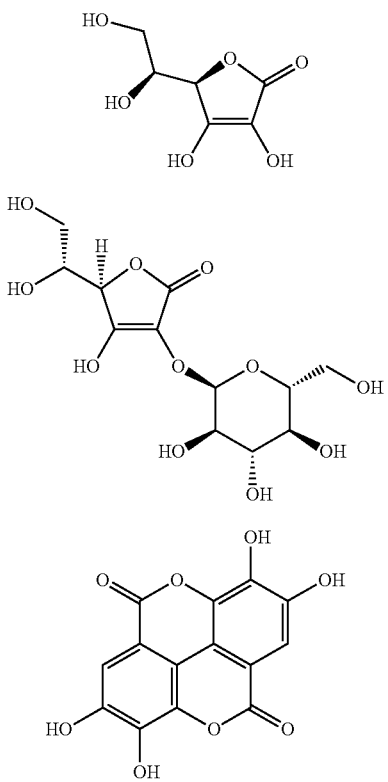

Examples of the five- or six-membered ring heterocyclic compound having a cyclic amide skeleton include γ-butyrolactam (B1), N-hydroxy-γ-butyrolactam, δ-valerolactam (B2), N-hydroxy-δ-valerolactam, and compounds having a protecting group (e.g., an acyl group, a sulfonyl group, a sulfate group, and a phosphate group) introduced to the hydroxyl groups of these compounds.

Preferably, the heterocyclic compound having a cyclic amide skeleton, and the heterocyclic compound having a cyclic imide skeleton are five- or six-membered ring compounds having 1 to 3 nitrogen atoms.

The following chemical structures represent examples of the five- or six-membered ring heterocyclic compounds having a cyclic amide skeleton.

[Chem. 2]

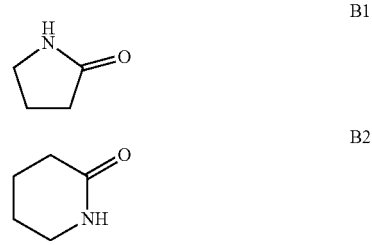

In the five- or six-membered ring heterocyclic compounds having a cyclic amide and a cyclic imide skeleton, the five-membered ring heterocyclic compound having a cyclic imide skeleton is a heterocyclic compound having one nitrogen atom as a heteroatom. Examples of such compounds include N-hydroxysuccinimide (C1), N-acetoxysuccinimide, N,N'-disuccinimidyl carbonate, N-carbobenzoxyoxysuccinimide, N-hydroxymaleimide, and compounds having a protecting group (e.g., an acyl group, a sulfonyl group, a sulfate group, and a phosphate group) introduced to the hydroxyl group of these compounds; phthalimide (C2), N-hydroxyphthalimide, N-acetylphthalimide (C4), N-(tert-butoxycarbonyloxy)phthalimide (C5), N-hydroxyhexahydrophthalimide, N,N'-dihydroxycyclohexanetetracarboxdiimide, and compounds having a protecting group (the same as above) introduced to the hydroxy group of these compounds; and N-methylmaleimide, N-methoxycarbonylmaleimide, N-maleimidobutyric acid, and compounds having a protecting group (e.g., an acyl group, a sulfonyl group, a sulfate group, and a phosphate group) introduced to the methyl group of these compounds. Most preferred are N-hydroxysuccinimide, N-acetoxysuccinimide (C6), N,N'-disuccinimidyl carbonate (C3), N-carbobenzoxyoxysuccinimide, phthalimide, N-acetylphthalimide, and N-(tert-butoxycarbonyloxy)phthalimide, optimally N-acetoxysuccinimide (C6), and N,N'-disuccinimidyl carbonate (C3).

The following chemical structures represent examples of the five-membered ring heterocyclic compound having a cyclic imide skeleton with one nitrogen atom contained as a heteroatom.

[Chem. 3]

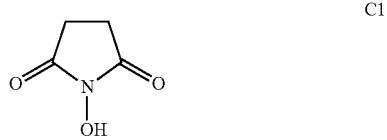

-continued

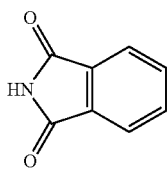
C2

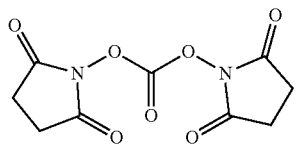
C3

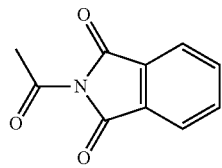
C4

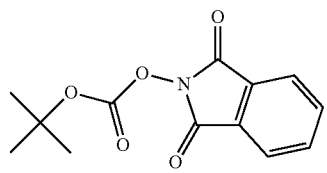
C5

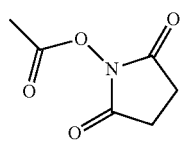
C6

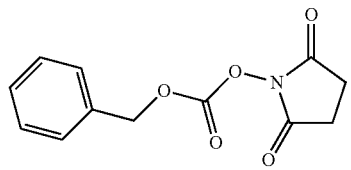
C7

Examples of the five-membered ring heterocyclic compound having a cyclic imide skeleton with two nitrogen atoms contained as heteroatoms include compounds having a hydantoin skeleton, for example, such as a hydantoin (D1), 3-hydroxy hydantoin, 1,3-dihydroxy hydantoin, 3-hydroxy-1-methyl hydantoin, and compounds having a protecting group (the same as above) introduced to the hydroxyl group of these compounds. Most preferred for use is the hydantoin.

The following chemical structure represents an example of the five-membered ring heterocyclic compound having a cyclic imide skeleton with two nitrogen atoms contained as heteroatoms.

[Chem. 4]

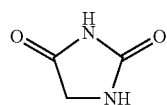
D1

Examples of the five-membered ring heterocyclic compound having a cyclic imide skeleton with three nitrogen atoms contained as heteroatoms include 1,2,4-triazolidine-3,5-dione (E1), 4-hydroxy-1,2,4-triazolidine-3,5-dione, 4-hydroxy-1,2,4-triazoline-3,5-dione, and compounds having a protecting group (e.g., an acyl group, a sulfonyl group, a sulfate group, and a phosphate group) introduced to the hydroxyl group of these compounds. The following chemical structure represents an example of the five-membered ring heterocyclic compound having a cyclic imide skeleton with three nitrogen atoms contained as heteroatoms.

[Chem. 5]

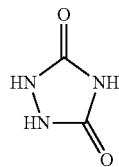
E1

Examples of the six-membered ring heterocyclic compound having a cyclic imide skeleton include compounds having one nitrogen atoms as a heteroatom, for example, such as a glutarimide (F1), N-hydroxy glutarimide, N-hydroxy naphthalimide, N,N'-dihydroxy-1,8,4,5-naphthalene tetracarboxdiimide, N-hydroxy-1,8-decalindicarboximide, N,N'-dihydroxy-1,8,4,5-decalin tetracarboxdiimide, and compounds having a protecting group (e.g., an acyl group, a sulfonyl group, a sulfate group, and a phosphate group) introduced to the hydroxyl group of these compounds. Most preferred is the glutarimide. The following chemical structure represents an example of these compounds.

[Chem. 6]

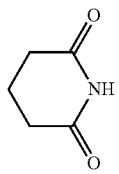
F1

Examples of the six-membered ring heterocyclic compound having a cyclic imide skeleton with two nitrogen atoms contained as heteroatoms include hexahydro-1,3-diazine-2,4-dione (G1), hexahydro-3-hydroxy-1,3-diazine-2,4-dione, hexahydro-1,3-dihydroxy-1,3-diazine-2,4-dione, hexahydro-1-hydroxy-1,3-diazine-2,4,6-trione, uracil, 3-hydroxy-uracil, and compounds having a protecting group (e.g., an acyl group, a sulfonyl group, a sulfate group, and a phosphate group) introduced to the hydroxyl group of these compounds. The following chemical structure represents an example of these compounds.

[Chem. 7]

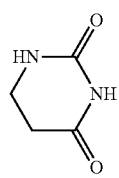
G1

Examples of the six-membered ring heterocyclic compound having a cyclic imide skeleton with three nitrogen atoms contained as heteroatoms include hexahydro-1,2,4- triazine-3,5-dione (H2), hexahydro-4-hydroxy-1,2,4-triazine-3,5-dione, and compounds having a protecting group (e.g., an acyl group, a sulfonyl group, a sulfate group, and a phosphate group) introduced to the hydroxyl group of these compounds. Other examples include hexahydro-1,3,5-triazine-2,6-dione (H1), hexahydro-1-hydroxy-1,3,5-triazine-2,6-dione, hexahydro-1-hydroxy-1,3,5-triazine-2,4,6-trione, hexahydro-1,3,5-trihydroxy-1,3,5-triazine-2,4,6-trione, and compounds having a protecting group (e.g., an acyl group, a sulfonyl group, a sulfate group, and a phosphate group) introduced to the hydroxyl group of these compounds. The following chemical structures represent examples of these compounds.

[Chem. 8]

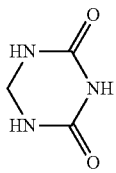

H1

-continued

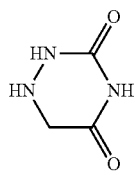

H2

Examples of the six-membered ring heterocyclic compound having a cyclic imide skeleton with four nitrogen atoms contained as heteroatoms include hexahydro-1,2,3,5-tetrazine-4,6-dione (I1), hexahydro-5-hydroxy-1,2,3,5-tetrazine-4,6-dione, and compounds having a protecting group (e.g., an acyl group, a sulfonyl group, a sulfate group, and a phosphate group) introduced to the hydroxyl group of these compounds. The following chemical structure represents an example of these compounds.

[Chem. 9]

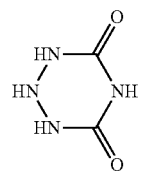

I1

The present inventors conducted studies by impregnating two sample pads of an immunochromatographic kit with sodium nitrite and citric acid, respectively, and found that increasing the amount of impregnated citric acid causes non-specific color production, and poor extraction efficiency, though the procedure was simple, and the assay repeatability improved. In order to solve this problem, a gold nanoparticle dispersion was produced by mixing antibody-immobilized gold colloids, sodium nitrite, and various organic acids or organic compounds, and the extent of nitrous acid generation, and particle dispersibility were evaluated by visual inspection. The results are presented in Table 1.

The visual evaluation of the extent of nitrous acid gas generation can be made according to the following criteria.

−: No generation is observable by visual judgment

+: Slight generation is observable

++: Generation is clearly observable

+++: Large generation is observable

TABLE 1

| | Citric acid | Itaconic acid | Aspartic acid | Glutamic acid | Ascorbic acid | N-Hydroxy-succinimide |
|---|---|---|---|---|---|---|
| Nitrous acid gas | +++ | ++ | ++ | ++ | ++ | ++ |
| Au colloid dispersibility | Aggregated | Aggregated | Aggregated | Aggregated | Dispersed | Slightly aggregated |

As is clear from the results shown in Table 1, aggregation occurs when more than certain quantities of citric acid and other major organic acids are present, though the mechanism of action, which is presumably due to the adsorption of the excess organic acid by the gold colloids, remains unclear. Particularly, citric acid, which is a weak acid with a single hydroxyl group, has three carboxyl groups, and is known to have the property to form a chelate complex with metal ions, in addition to its advantage to generate large amounts of nitrous acid gas. The aggregation is also considered to be due to this property of citric acid forming a complex with the gold colloids.

In any event, ascorbic acid was less likely to cause aggregation of gold colloids after the generation of nitrous acid, as compared to the other organic acids. Aggregation was also less common with N-hydroxysuccinimide, which caused only limited aggregation of gold colloids after the generation of nitrous acid as compared with the other organic acids, though the extent of aggregation was not as small as that observed for ascorbic acid.

In the light of these results, an experimental immunochromatographic kit for *streptococcus* test was produced by impregnating the sample dropping section [2] with sodium nitrite, and the reagent retaining section [3] with citric acid and ascorbic acid. The kit was used to test a negative analyte (extractant) and a positive analyte (inactivated antigen $2\times10^6$ org/mL), and the result was evaluated by observing the test line after 5 minutes from dropping the analytes. The results are presented in Table 2.

TABLE 2

|  | Citric acid | Ascorbic acid |
|---|---|---|
| Extractant | – | – |
| Inactivated antigen (2 × 10$^6$ org/mL) | + | ++ |

As is clear from the results shown in Table 2, a darker test line was observed in the ascorbic acid system than in the system using citric acid.

The organic compound used for the extractant system retained in the organic compound-containing antigen extracting section (reagent retaining section [3]) in the present invention is a heterocyclic compound having at least one skeleton selected from the group consisting of a cyclic ester, a cyclic amide, and a cyclic imide, specifically, an organic compound that generates a nitrous acid by a contact reaction with a nitrite salt, without causing denaturation or precipitation of proteins or other materials present in the test device.

The heterocyclic compound having at least one skeleton selected from the group consisting of a cyclic ester, a cyclic amide, and a cyclic imide is used in a molar ratio of 0.05 to 100:1 to 500 with respect to the nitrite salt.

The heterocyclic compound having at least one skeleton selected from the group consisting of a cyclic ester, a cyclic amide, and a cyclic imide is used in an amount of preferably 0.1 to 100 μmol, more preferably 0.1 to 50 μmol, further preferably 0.1 to 30 μmol, optimally 1 to 15 μmol per measurement (per kit). The nitrite salt is used in an amount of most preferably 10 to 100 μmol per measurement (per kit).

When a cyclic oligosaccharide is used in the present invention, the cyclic oligosaccharide may be contained in the immunochromatographic sample extractant (hereinafter, also referred to as "development extractant") or in the analyte diluting solution (hereinafter, also referred to as "analyte processing solution"), or may be contained in a different reagent retaining section [2] in the immunochromatographic kit. The cyclic oligosaccharide also may be contained in both of these locations, or any other location, as long as the cyclic oligosaccharide can exhibit its function. However, it is preferable for a functionality view point to contain the cyclic oligosaccharide in the analyte processing solution, which represents an early stage of development, or in a location on the upstream side of development.

An immunoassay method for detecting gram-positive bacteria in an analyte using the immunochromatographic kit of the present invention includes the steps of:

(i) contacting and mixing the analyte with an analyte diluting solution containing a buffer and a surfactant to produce an analyte diluting solution mixture;

(ii) feeding the analyte processing solution mixture to the sample dropping section;

(iii) developing the analyte processing solution mixture on the immunochromatography medium, and extracting antigens in the gram-positive bacteria with the nitrous acid generated on the medium by the reaction of the organic compound and the nitrite compound present in the antigen extracting section;

(iv) labeling the antigens in the label-substance retaining section;

(v) moving the labeled antigens on the chromatographic medium, and detecting the labeled antigens in the detection section; and (vi) absorbing the analyte processing solution mixture in the absorbing section.

Examples of the non-ionic surfactants that can be used in the immunochromatographic analyte diluting solution or in the reagent of the immunochromatographic kit in the present invention include polyoxyethylene alkyl ethers, polyoxyethylene/polyoxypropylene alkyl ethers, polyoxyethylene sorbitan fatty acid esters (trade name "Tween" series), polyoxyethylene-p-t-octylphenyl ethers (trade name "Triton" series), polyoxyethylene-p-t-nonylphenyl ethers (trade name "Triton N" series), alkyl polyglucosides, fatty acid diethanol amides, and alkylmonoclyceryl ethers. Other surfactants, for example, ionic surfactants, also may be used by being mixed with the non-ionic surfactants, provided that such addition does not cause any adverse effect.

The organic compound-containing antigen extracting section in the immunochromatographic kit of the present invention requires a surfactant for uniform development. However, the storage stability of the antigen extracting section is known to deteriorate when surfactants are contained.

To find a solution to this problem, a severe condition test (80° C., 12 hours) was conducted with a kit having an antigen extracting section containing various surfactants. As a result of the test, the preferred surfactants were found to be polyoxyethylene-p-t-octylphenyl ethers (trade name "Triton" series), for example, polyoxyethylene (10)-p-t-octylphenyl ether (trade name Triton X-100, HLB=13.5), Triton X-114 (trade name; HLB=12.4), and polyoxyethylene-p-t-nonylphenyl ether (trade name "Triton N" series), most preferably polyoxyethylene(10)-p-t-octylphenyl ether (trade name Triton X-100).

The non-ionic surfactant used for the analyte diluting solution and the immunochromatographic reagent in the present invention may be contained in an amount of 0.01 to 10 weight %. Preferably, the non-ionic surfactant may be contained in the immunochromatographic reagent in a content of 0.05 to 5 weight %.

Accurate determination is not possible with a content of less than 0.01 weight %, for example, 0.005 weight %. With a content of less than 0.05 weight %, non-specific reactions cannot be inhibited, and accurate determination is not always possible. A content of 10 weight % or more, for example, 12 weight %, and 18 weight %, is an excess concentration, and does not produce any favorable effect in inhibiting non-specific reactions. Such a concentration is also technically meaningless, and economically wasteful.

Examples of the salts used in the immunochromatographic reagent, for example, the extracting and developing solution, and the analyte processing solution in the present invention include sodium chloride, potassium chloride, calcium chloride, and magnesium chloride. The preferred salt is sodium chloride.

The salt contained in the immunochromatographic reagent, for example, the extracting and developing solution in the present invention is used in a concentration of typically 1 mM to 500 mM, preferably 5 mM to 200 mM, more preferably 10 mM to 50 mM.

Protein extraction becomes insufficient with a salt concentration of less than 1 mM, for example, 0.1 mM. A concentration of 500 mM or higher, for example, 1 M, and 2 M, is technically meaningless. Such a high salt concentration is uneconomical as the salt will be used in excess, and wasted.

The salt used in the immunochromatographic reagent in the present invention may be used alone or as a mixture of two or more.

The buffer used in the extracting and developing solution in the present invention is not particularly limited, as long as it does not produce a critical response to concentration changes such as by addition of a sample, or evaporation and dilution of a sample, or to entry of small amounts of foreign materials from outside (as long as the buffering effect remains intact).

Examples of the buffer that can be used in the present invention include phosphoric acid buffer (phosphoric acid+sodium phosphate), acetic acid buffer (acetic acid+sodium acetate), citric acid buffer (citric acid+sodium citrate), borate buffer, trishydrochloric acid buffer (tris(hydroxylmethyl) aminomethane+hydrochloric acid), TE buffer (tris+ethylenediaminetetraacetic acid), TAE buffer (tris+acetic acid+ethylenediaminetetraacetic acid), TBE buffer (tris+boric acid+ethylenediaminetetraacetic acid) or HEPES buffer (2-[4-(2-hydroxyethyl)-1-piperazinyl]ethanesulfonic acid), and Bicine buffer (N,N-bis(2-hydroxyethyl)glycine buffer).

Preferred examples include phosphoric acid buffer, trishydrochloric acid buffer, and acetic acid buffer, more preferably trishydrochloric acid buffer. In the immunochromatographic detection system of the present invention, two or more buffers may be used, as long as it does not produce any adverse effect.

The buffer concentration used in the present invention is preferably 10 to 500 mM, more preferably 10 to 300 mM, further preferably 30 to 100 mM. With a concentration of less than 10 mM, the buffering effect becomes insufficient, and precipitation of a protein component, and aggregation of labeled particles become insufficiently inhibited. A concentration of 500 mM and higher is an excess concentration, and economically wasteful. Optimally, the buffer is brought to a pH of 7.1 to 9.8.

In the immunochromatographic reagent of the present invention, it is possible and effective to add additives that are known to inhibit side reaction due to biological affinity, and non-specific reactions. Specifically, it is possible to add one or more additives that promote antigen-antibody reaction, or inhibit non-specific reaction, for example, such as proteins (for example, bovine serum albumin, gelatin, casein), polymeric compounds (for example, polyethylene glycol, methyl cellulose, polyvinylpyrrolidone, polyvinyl alcohol, dextran), ionic surfactants or polyanions (for example, dextransulfuric acid, heparin, polystyrene sulfonate, chondroitin sulfate), and antimicrobial agents. Use of these additives does not pose any problem.

One or more of these proteins, polymeric compounds, ionic surfactants or polyanions, or antimicrobial agents for promoting antigen-antibody reaction or inhibiting non-specific reaction may be retained on the traveling path of a mobile phase on the chromatographic medium constituting a stationary phase. This is also effective, and does not pose any problem.

The concentration of the additive contained in the immunochromatographic reagent composition of the present invention is preferably 0.01 to 20 weight %, more preferably 0.1 to 10 weight %, further preferably 0.5 to 5 weight %. Non-specific reactions cannot be inhibited, and accurate determination is not possible with a concentration of less than 0.01 weight %. A concentration of more than 20 weight % is an excess concentration, and is economically wasteful.

The immunochromatographic reagent of the present invention has optimum use as a developer, and may preferably be used also as a diluting solution for an analyte sample.

Use of the immunochromatographic reagent is not limited to these, and the immunochromatographic reagent may be used in such a form that the component of the immunochromatographic reagent is provided on the traveling path of a mobile phase on the immunochromatography medium.

When the immunochromatographic reagent is used as a developer or a diluting solution, typically, water is used as a solvent, and a buffer, a protein, a salt, and a non-ionic surfactant are added thereto. These may be added in non-specific order, and may be added simultaneously. When the immunochromatographic reagent is used as a developer or a diluting solution, a premixture of these solutions with a sample (analyte) to be detected may be fed and dropped on the sample dropping section for development, or the developer may be fed and dropped on the sample dropping section for development after feeding and dropping a sample (analyte) on the sample pad (sample dropping section).

When the immunochromatographic reagent of the present invention is used by being provided on the traveling path of a mobile phase on the immunochromatography medium, the immunochromatographic reagent, in an exemplary form, may be retained by being supported or retained in the sample dropping section by using a method whereby, for example, the immunochromatographic reagent is dried after being applied or impregnated in the sample dropping section of the immunochromatography device.

In another form of retaining or supporting the immunochromatographic reagent of the present invention on the immunochromatography medium, the immunochromatographic reagent may be retained in an additive (reagent) retaining section provided anywhere between the end of the sample dropping section and the absorbing section. For example, the immunochromatographic reagent may be retained on the sample dropping section, the label-substance retaining section, or the immunochromatography medium.

The detection target in the present invention is not particularly limited, as long as a substance that specifically binds to the detection target, for example, such as by antigen-antibody reaction, is present or can be produced. The detection target may itself have antigenicity, as in the case of a complete antigen, or may not have antigenicity by itself but may acquires antigenicity by being chemically modified, as in the case of a hapten (incomplete antigen). Whether it is present or can be produced, the substance that specifically binds to the detection target may be a monoclonal antibody or a polyclonal antibody.

The detection target in the present invention is a polysaccharides antigen that is specific to the detection target, and that can be extracted with the generated nitrous acid. Examples include gram-positive bacteria having a thick peptidoglycan layer. Preferred are cocci, particularly preferably bacterial antigens such as *streptococcus* antigens.

The analyte that is optimum to the present invention is a nasal discharge, a nasal swab, a pharyngeal swab, or phlegm. By diluting such an analyte with the analyte diluting solution of the present invention in advance, and feeding the analyte to the test device for extraction, the *streptococcus* antigen collected from, for example, a respiratory disease patient, can be accurately detected as a target material.

The immunochromatographic kit of the present invention is an immunochromatographic kit for detecting gram-positive bacteria in a sample, and is configured from an analyte diluting solution (analyte processing solution); and an immunochromatographic device that includes a sample dropping section, an antigen extracting section, a label-substance retaining section, a chromatographic medium having a detection section, and an absorbing section.

In the immunochromatographic kit, a nitrite salt and/or a cyclic oligosaccharide are contained in at leas one of the analyte diluting solution and the sample dropping section, either alone or in combination. That is, the immunochromatographic kit includes a nitrite salt, or a nitrite salt and a cyclic oligosaccharide.

The immunochromatographic kit is an immunochromatographic kit that includes the antigen extracting section where a nitrous acid is generated by a contact reaction between the nitrite salt, and the heterocyclic compound having at least one skeleton selected from the group consisting of a cyclic ester, a cyclic amide, and a cyclic imide retained in the antigen extracting section.

The immunochromatographic kit may contain 0 to 20 µg of a cyclic oligosaccharide per immunochromatographic kit. In the immunochromatographic kit, the sample dropping section [2] and the antigen extracting section [3] constituting the kit are disposed upstream of the label-substance retaining section [4] in the direction of development.

The structure of the immunochromatographic kit for detecting a target material in an analyte, and the operation and detection technique are known.

Testing of the target material in an analyte by antigen-antibody reaction, such as in identification and quantification, is possible by dropping an analyte sample into the sample dropping section of a conventional immunochromatographic kit after the analyte sample is prepared by diluting an analyte with the analyte processing solution of the present invention, and extracting the antigens in the analyte by developing the sample on the immunochromatography medium toward the absorbing section.

The immunochromatographic kit is described below.

The immunochromatographic kit is configured typically from an immunochromatographic device (also referred to as "immunochromatography device"), and a sample extractant [6], wherein the immunochromatographic device includes a chromatographic medium [1] (having the "detection section (determining section)"), a sample dropping section [2] (also referred to as "sample pad", or "reagent retaining section [2]"), an organic compound-containing antigen extracting section [3] (also referred to as "reagent retaining section [3]", or simply "antigen extracting section"), a label-substance retaining section [4], an absorbing section [5](also referred to as "development rate control section"), and a backing sheet [7].

The immunochromatographic device is described below.

FIGS. 1A and 1B show a device structure that has been modified to properly perform the immunochromatographic detection method, that is to implement the component of the immunochromatographic reagent on the immunochromatography medium according to the present invention, specifically a structure for improving antigen extraction efficiency. The device is described below with reference to FIGS. 1A and 1B.

The structure of the device shown in FIGS. 1A and 1B is configured from 1) a chromatographic medium [1], 2) a reagent retaining section [2] (or collectively, a sample pad), 3) a reagent retaining section [3] (or collectively, an organic compound-containing antigen extracting section, or simply "antigen extracting section"), 4) a label-substance retaining section [4] (or collectively, a conjugate pad), 5) an absorbing section [5], and 7) a backing sheet. The immunochromatography device of the present invention has a structure configured from at least these elements 1 to 5.

Among the findings of the present invention is that the order of the constituting elements affects the performance.

The following example compares the order of the constituting elements of the structure, and its effect on development between two structures.

| | | | | | |
|---|---|---|---|---|---|
| Structure of present invention (1) | 2 | 3 | 4 | 1 | 5 Desirable development |
| Comparative structure (2) | 3 | 2 | 4 | 1 | 5 Undesirable development |

As the result of the comparison above indicates, different orders of the constituting elements 1 to 5 have different effects on the behavior, particularly development. In a combination of the constituting elements, the most preferred form in the present invention is when these elements are combined in the order of development shown in FIGS. 1A and 1B. When developability is not of priority, the structure may have a different order of constituting elements.

The immunochromatographic device is basically a testing tool formed by the constituting elements shown in FIGS. 1A and 1B. However, omitting the 3) reagent retaining section [3] in particular necessitates the complicated preparation of nitrous acid immediately before use, and prevents smooth testing.

As described above, the present inventors have found that the immunochromatographic device as shown in FIGS. 1A and 1B is highly functional in terms of test performance, and ease of handling in a test.

The sample dropping section [2], and the reagent retaining section [3] are configured from porous sheets such as glass filter papers of a property that quickly absorbs a sample, but has only weak retention so that the sample quickly moves to the reaction section.

The sample dropping section [2] may contain a nitrite salt, which generates a nitrous acid by reacting with the organic compound contained in the reagent retaining section [3]. However, the nitrite salt may instead be contained in the analyte diluting solution [2], or may be contained in both the analyte diluting solution and the sample dropping section [2]. The nitrite salt can effectively exhibit its function when contained upstream of the organic compound-containing site in the direction of development.

The analyte diluting solution may contain a cyclic oligosaccharide. However, the cyclic oligosaccharide may instead be contained in the sample dropping section [2], or may be contained in both the analyte diluting solution and the sample dropping section [2]. The nitrite salt can effectively exhibit its function when contained upstream of the organic compound-containing site in the direction of development.

The reagent retaining section [3] serves as an antigen extracting section, and to this end contains an organic compound including ascorbic acid and/or N-hydroxysuccinimide. For uniform development, the reagent retaining section [3] also contains a non-ionic surfactant, specifically Triton X-100 (trade name) or Triton X-114 (trade name). This also improved storage stability.

The label-substance retaining section [4] retains a label reagent labeling a reagent component with a label component. The label component may be, for example, a metal particle, a latex particle, an enzyme, or a fluorescent compound, of which a metal particle is optimum. Particularly preferred is a metal nanoparticle carrier. The reagent component is a particle or a molecule capable of recognizing the analyte. Preferably, the reagent component is a monoclonal antibody or a polyclonal antibody, or a fragment thereof (second reagent).

Preferred for use as metal particles are, for example, single or composite particles of noble metals such as gold, silver, platinum, germanium, rhodium, and palladium. Most preferred is gold for its sensitivity to color changes.

With regard to the form of metal particles, the average particle size is about 1 to 500 nm, preferably about 10 to 250 nm, more preferably about 35 to 100 nm. Preferably, the metal particles are contained in a concentration of about 0.0001 to 0.08 weight %, preferably about 0.002 to 0.06 weight % with respect to the medium.

As used herein, "metal nanoparticles" refers to particles of metals having nano diameters in the foregoing range of average particle size. For immunoassay, platinum particles may be supported on the metal particle surface to form metal composite particles, taking into account factors such as the particle size, the particle size distribution, and the color of the metal, and the metal composite particles may be used as an immunoassay label to improve usefulness as a protein staining dye. Measurement sensitivity can further improve when a sensitizer, such as a metal label enhancer having a functional group capable of binding to the metal particle surface, and a reactive group capable of binding to an antibody is used.

The chromatographic medium [1] has a detection section produced on a membrane carrier. The membrane carrier is not particularly limited, as long as it can absorb and move the sample analyte by capillary action. For example, the membrane carrier is selected from the group consisting of synthetic polymers formed of nitrocellulose, cellulose acetate, nylon, polyether sulfone, polyvinyl alcohol, polyester, glass fiber, polyolefin, cellulose, and a mixed fiber thereof.

The detection section includes monoclonal antibodies, polyclonal antibodies, or fragments thereof (first reagent) supported and immobilized on a nitrocellulose sheet.

The absorbing section [5] commonly uses filter paper formed from a glass fiber, a cellulose fiber, and other such materials capable of quickly absorbing excess samples. It is more preferable to use materials capable of retaining the absorbed liquid so that there is no back-flow of the liquid (JP-A-2012-189346).

The backing sheet [7] is a substrate. One surface of the backing sheet [7] is rendered adhesive by applying an adhesive agent, or by attaching an adhesive tape. On the adhesive surface are provided the sample adding section [2], the antigen extracting section [3], the label-substance retaining section [4], the chromatographic medium [1] having the detection section, and the absorbing section [5], in contact with the adhesive surface either in part or as a whole. The backing sheet [7] as a substrate is not particularly limited, as long as the substrate, with an adhesive agent, is impermeable to the sample solution and moisture.

The detection reagent (first reagent) used for the detection section, and the detection reagent (second reagent) used for the label reagent are capable of binding the antigens of the detection target in an analyte. The detection reagents are, for example, antibodies. When the detection reagents are antibodies, either the detection reagent (first reagent) used for the detection section, or the detection reagent (second reagent) used for the label reagent may be monoclonal antibodies or polyclonal antibodies, or both of these detection reagents may be monoclonal antibodies or polyclonal antibodies.

The monoclonal antibodies, the polyclonal antibodies, and fragments thereof are known and available, and may be prepared using known methods. Examples of antibody-producing animal species include human, mouse, rat, rabbit, goat, and horse. Preferably, the monoclonal antibodies, the polyclonal antibodies, and fragments thereof are antibodies derived from at least one animal species selected from rabbit, goat, and mouse. The immunoglobulin may be NG; IgM, IgA, IgE, or IgD.

In the Examples of the present invention below, a rabbit-derived anti-*streptococcus* polyclonal antibody is used as the reagent component (second reagent) used for the label reagent, and a rabbit-derived anti-*streptococcus* monoclonal antibody is used for the reagent component (first reagent) used for the detection section. However, the invention is not limited to this. It is also possible to use rabbit-derived anti-*streptococcus* polyclonal antibodies or rabbit-derived anti-*streptococcus* monoclonal antibodies for both of these reagents.

The following is a general overview of the principle behind the determination performed with a typical kit configuration.

1. An analyte diluting solution mixture prepared by diluting an analyte (sample) with the analyte diluting solution [6] is dropped on the sample dropping section [2] in a predetermined amount (typically, 0.1 to 2 ml). Upon being dropped, the analyte diluting solution mixture becomes quickly absorbed by the sample dropping section [2], and immediately starts moving at the same time. The reagent composition containing a nitrite salt, or a nitrite salt and a cyclodextrin, retained in the sample dropping section [2] in dry from dissolves in the water component of the analyte diluting solution mixture, and starts moving with the analyte (sample).

2. The analyte diluting solution mixture with the dissolved nitrite salt first moves to the antigen extracting section [3]. Here, the dry organic compound retained in the antigen extracting section [3] undergoes a contact reaction with the nitrite salt dissolved in the incoming analyte diluting solution mixture, and generates a nitrous acid. When streptococci are present in the analyte (sample), the nitrous acid extracts the polysaccharides on the bacteria surface.

3. The analyte diluting solution mixture containing the generated nitrous acid then moves to the label-substance retaining section [4] in a uniform and smooth fashion. While the analyte diluting solution mixture is passing through the label-substance retaining section [4], the label reagent (second reagent) retained in the label-substance retaining section [4] dissolves into the water component of the analyte diluting solution mixture, and moves with the analyte (sample).

4. The label reagent dissolved in the water component of the analyte diluting solution mixture passes through the detection site on the chromatographic medium [1]. Here, the immunochromatographic reagent composition dissolved in the analyte diluting solution mixture inhibits non-specific binding reaction, and, when the target material (for example, polysaccharides) is present in the analyte diluting solution mixture, the label reagent undergoes a specific antigen-antibody reaction, and specifically in sandwich condition binds between the antibodies and the label reagent supported and immobilized on the detection site. In response, the detection section produces a color. When the target material (for example, polysaccharides) is absent in the analyte sample, the detection site does not produce a color because the label reagent dissolved in water component of the analyte diluting solution mixture does not undergo a specific binding reaction upon passing through the detection section on the chromatographic medium [1].

5. Finally, the water component of the analyte diluting solution mixture moves to the absorbing section [5].

The presence or absence of a target material (for example, polysaccharides) in an analyte (sample) can be accurately determined in the manner described above.

EXAMPLES

The effectiveness of the present invention is described below with reference to Examples. The present invention, however, is not limited to the following. The present invention is an immunochromatographic kit that includes a sample dropping section [2] containing sodium nitrite; an antigen extracting section [3] containing ascorbic acid as a representative compound that belongs to the domain of the five- or six-membered ring heterocyclic compound having a cyclic ester skeleton; and an absorbing section [5] formed of a development rate control member (absorption rate of 80 to 200 mg/cm$^2$) provided to optimize extraction efficiency.

Example 1

(1) Production of Detection Section on Chromatographic Medium [1]

A nitrocellulose sheet (Millipore; trade name: HF120; 250 mm×25 mm) was used as a membrane. A rabbit-derived anti-*streptococcus* monoclonal antibody (first antibody) was diluted to a concentration of 1.0 mg/ml with a 10 mM phosphoric acid buffer (pH 7.4) containing 5 mass % isopropanol, and 150 μL of the diluted solution was applied onto the membrane over a 1-mm width using an antibody applicator (BioDot). The solution was dried at 50° C. for 30 min, and dried overnight at room temperature to produce the detection section on the chromatographic medium [1].

(2) Production of Label Substance Solution

For the production of a label substance solution, 0.1 mL of rabbit-derived anti-*streptococcus* polyclonal antibodies (second antibody) that had been diluted to a concentration of 0.1 mg/mL with phosphoric acid buffer (pH 7.4) was added to 0.5 mL of a gold colloid suspension (Tanaka Kikinzoku Kogyo; average particle size 40 nm), and the mixture was allowed to stand at room temperature for 10 min. Thereafter, 0.1 mL of a phosphoric acid buffer (pH 7.4) containing 10 mass % bovine serum albumin was added, and the mixture was thoroughly stirred, and centrifuged at 8000×g for 15 min. After removing the supernatant, 0.1 mL of a phosphoric acid buffer (pH 7.4) containing 1 mass % bovine serum albumin was added to produce a label substance solution.

(3) Production of Reagent Retaining Section [2] Containing Sodium Nitrite and Cyclic Oligosaccharide For the production of reagent retaining section [2], 0.6 mL of an aqueous solution containing 1 mmol of sodium nitrite, and 2 μmol of β-cyclodextrin was applied to a 12×100 mm glass fiber conjugate pad (Merck), and freeze dried to produce the reagent retaining section [2].

(4) Production of Reagent Retaining Section [3] Containing Ascorbic Acid

For the production of reagent retaining section [3], 0.6 mL of a 1.7 mass % aqueous solution of non-ionic surfactant Triton-X100 containing 50 μmol of ascorbic acid was applied to a 12×100 mm glass fiber conjugate pad (Merck), and freeze dried to produce the reagent retaining section [3].

(5) Production of Test Piece for Immunochromatography

For production of a test piece, 100 μl of a 25 mass % trehalose aqueous solution, and a phosphoric acid buffer (pH 9.0) containing 80 μl of 5 mass % casein (final concentration: 1 mass %) were added to 200 μl of the label substance solution produced above, and the mixture was uniformly added to a 12×100 mm glass fiber pad (Millipore). The solution was then dried with a vacuum dryer to produce the label-substance retaining section [4]. The absorbing section [5] for absorbing the developed sample and the label substance, the chromatographic medium [1] having the determination section produced above, the label-substance retaining section [4], the reagent retaining section [2], and the reagent retaining section [3] were then attached to a substrate backing sheet in the order shown in Table 1 from the upstream side of immunochromatography development (from the right to left). The product was then cut into a 5-mm width with a cutting machine to obtain a test piece for immunochromatography.

(6) Production of Analyte Diluting Solution

An analyte containing 0.5 mass % Tween 20, a 0.6 mass % polyvinylpyrrolidone (average molecular weight of 360,000), and a 20 mM tris buffer solution (pH 8.0) containing 1 mass % bovine serum albumin and 150 mM sodium chloride was diluted to obtain an analyte diluting solution to be added to the immunochromatography test piece for development.

(7) Measurement

The immunochromatography test piece, and the analyte diluting solution produced above were used to measure the presence or absence of antigen streptococci in the analyte, as follows. Specifically, an analyte diluting solution containing no antigen was used as a negative analyte sample, and a negative analyte sample with 2×10$^6$ org/mL of inactivated group A β hemolytic *streptococcus* (*streptococcus*) was used as a positive analyte sample.

The negative analyte sample and the positive analyte sample (150 μL each) were added to the most upstream side of the immunochromatography test piece in the direction of development. Specifically, on the reagent retaining section [2] in Examples 1 and 2; on the reagent retaining section [3] in Comparative Examples 1 and 2; and on the label-substance retaining section [4] in Comparative Example 3 and Example 3. After 15 minutes of development, the test piece was visually inspected to make determination. The test piece was "+" when a red line was observed on the test line, "++" when the red line was clearly visible, "±" when a red line was observed but the color was very thin, and "−" when a red line was not observable. For the evaluation of developability, development was determined as undesirable when the developer did not flow onto the chromatographic medium, or when the developer developed to the chromatographic medium but when there was no flow of the label reagent. Development was also determined as undesirable when the leading end of the solution had an irregular shape during the development on the chromatographic medium. Samples that did not fall into any of these categories were determined as desirable. The results are presented in Table 3.

The test is conducted under the following conditions.
Positive: 4×10$^5$ org/mL *streptococcus* (test time: 8 min)
Negative: developer (test time: 30 min)

TABLE 3

| | Order of attachment* (from upstream to downstream of development direction) | Antigen amount in positive analyte | Developability | Determination |
|---|---|---|---|---|
| Ex. 1 | 2-3-4-1-5 | 2 × 10$^6$ org/mL | Desirable | + |
| Ex. 2 | 2-4-3-1-5 | | Desirable | + |
| Com. Ex. 1 | 3-2-4-1-5 | | Undesirable | |

TABLE 3-continued

| | Order of attachment* (from upstream to downstream of development direction) | Antigen amount in positive analyte | Developability | Determination |
|---|---|---|---|---|
| Com. Ex. 2 | 3-4-2-1-5 | | Undesirable | |
| Com. Ex. 3 | 4-3-2-1-5 | | Undesirable | |
| Ex. 3 | 4-2-3-1-5 | | Desirable | + |

The numbers 1 to 5 in the table indicate chromatographic medium [1], reagent retaining section [2], reagent retaining section [3], label-substance retaining section [4], and absorbing section [5], respectively.

In Examples 1 to 3 in which the reagent retaining section [3] containing ascorbic acid was on the downstream side of the reagent retaining section [2] in the direction of development, the protein component in the sample was not affected by the acid, and the development was desirable.

Development was undesirable in Comparative Examples 1 to 3. This is probably the result of the ascorbic acid-containing reagent retaining section [3] being on the upstream side of the reagent retaining section [2] in the direction of development, causing clogging as a result of the acid-induced precipitation of the protein component in the sample. As these test results indicate, the reagent retaining section [2] is required to be on the upstream side of the reagent retaining section [3] in the direction of development.

The test conducted in Example 1 was repeated using the same procedure, except that the reagent retaining section [3] contained N-hydroxysuccinimide, instead of ascorbic acid. The result was determined by visual inspection using the same criteria. The result was essentially the same, except that the color of the test line was slightly thinner than that observed in Example 1.

The test conducted in Example 1 was repeated using the same procedure, except that the reagent retaining section [2] did not contain sodium nitrite, but potassium nitrite was added to the analyte diluting solution in an amount of 50 µmol/test. The result was determined by visual inspection using the same criteria. The result was essentially the same as in Example 1.

The immunochromatographic kit of Example 1 is configured so that the reagent retaining section [2] contains β-cyclodextrin (hereinafter, simply "β-CD"). However, an immunochromatographic kit containing no CD was also produced.

The test conducted in Example 1 was repeated using the same procedure, except that γ-cyclodextrin, amino-β-cyclodextrin (short for "3A-amino-3A-deoxy-(2AS,3AS)-β-cyclodextrin hydrate"), and m-β-cyclodextrin (short for "6-0-α-D-maltosyl-β-cyclodextrin (molecular weight 1,459)") were added instead of β-CD. The result was determined by visual inspection using the same criteria. The result was essentially the same as in Example 1. The CDs were retained in the nitrite containing section in an amount of 0.75 µg/test each.

Examples 4 to 6

The test conducted in Example 1 was repeated using the same procedure, using sodium nitrite, cyclic cyclodextrin, and ascorbic acid in the amounts per test shown in Table 4. An analyte (150 µL) containing $2 \times 10^6$ org/mL of inactivated *streptococcus* per test was used as a positive analyte. The result was determined by visual inspection using the same criteria. The results are presented in Table 4.

Examples 7 to 10

A nitrite salt, cyclic cyclodextrin, and ascorbic acid and/or N-hydroxysuccinimide were used in the amounts per test shown in Table 4.

Example 7

The test conducted in Example 1 was repeated using the same procedure, except that the reagent retaining section [3] contained N-hydroxysuccinimide, a compound that belongs to the domain of the five-membered ring heterocyclic compound having a cyclic imide skeleton, instead of ascorbic acid. The result was determined by visual inspection using the same criteria. The results are presented in Table 4.

Example 8

The test conducted in Example 1 was repeated using the same procedure, except that the reagent retaining section [2] did not contain sodium nitrite, but potassium nitrite was added to the analyte diluting solution in an amount of 50 µmol/test. The result was determined by visual inspection using the same criteria. The results are presented in Table 4.

Example 9

The test conducted in Example 1 was repeated using the same procedure, except that β-cyclodextrin was not contained in the reagent retaining section [2], but was contained in the analyte diluting solution. The result was determined by visual inspection using the same criteria. The results are presented in Table 4. Examples 8 and 9 represent an implementation in which a nitrite salt or a cyclic oligosaccharide is retained in the analyte diluting solution.

Example 10

The test conducted in Example 1 was repeated using the same procedure, except that the reagent retaining section [2] did not contain β-cyclodextrin or sodium nitrite, but 50 µmol of potassium nitrite, and 0.1 µmol of β-cyclodextrin were added to the analyte diluting solution. The result was determined by visual inspection using the same criteria. The results are presented in Table 4. Example 10 represents an implementation in which a nitrite salt and a cyclic oligosaccharide are retained in the analyte diluting solution.

TABLE 4

| | Sodium nitrite amount (μmol/test) | Ascorbic acid amount (μmol/test) | Cyclic oligosaccharide, and amount (μmol/test) | Analyte | Determination (N = 5) | | | | |
|---|---|---|---|---|---|---|---|---|---|
| Ex. 4 | 50 | 1 | — 0 | Positive analyte*1 | ++ | ++ | ++ | ++ | ++ |
| | | | | Negative analyte | ± | − | ± | − | − |
| Ex. 5 | 10 | 1 | β-CD 0.1 | Positive analyte*1 | + | + | + | + | + |
| | | | | Negative analyte | − | − | − | − | − |
| Ex. 6 | 100 | 1 | β-CD 0.02 | Positive analyte*1 | ++ | ++ | ++ | ++ | ++ |
| | | | | Negative analyte | − | − | − | − | − |
| Ex. 7 | 50 | 0.1*2 | γ-CD 0.1 | Positive analyte*1 | + | + | + | + | + |
| | | | | Negative analyte | − | − | − | − | − |
| Ex. 8 | 50*3 | 1 | γ-CD 0.1 | Positive analyte*1 | ++ | ++ | ++ | +++ | +++ |
| | | | | Negative analyte | − | − | − | − | − |
| Ex. 9 | 50 | 4 | β-CD*4 0.1 | Positive analyte*1 | +++ | ++ | ++ | +++ | +++ |
| | | | | Negative analyte | − | − | − | − | − |
| Ex. 10 | 50*3 | 2 | β-CD*4 0.1 | Positive analyte*1 | +++ | +++ | +++ | +++ | +++ |
| | | | | Negative analyte | − | − | − | − | − |

*1 150 μL of inactivated *streptococcus* was used as a positive analyte in a concentration of 2 × 10$^6$ org/mL per test.
*2 N-hydroxysuccinimide was used instead of ascorbic acid.
*3 Potassium nitrite was used instead of sodium nitrite. Potassium nitrite was added to the analyte diluting solution, without being added to the reagent retaining section [2].
*4 Cyclic oligosaccharide was added to the analyte diluting solution, without being added to the reagent retaining section [2].

As can be seen from the results shown in Table 4, Examples 8 to 10 in which the nitrite salt and/or the cyclic oligosaccharide were added to the analyte diluting solution without being added to the reagent retaining section [2] produced much more desirable results than Examples 5 to 7 in which the nitrite salt and/or the cyclic oligosaccharide were added to the reagent retaining section [2].

Examples 11 to 19

The test conducted in Example 1 was repeated using the same procedure, except that the reagent retaining section [3] contained an organic compound having a cyclic ester skeleton, a cyclic amide skeleton, or a cyclic imide skeleton, instead of ascorbic acid. The result was determined by visual inspection using the same criteria. The results are presented in Table 5. The test conducted in Example 1 was repeated using the same procedure, except that the reagent retaining section [3] contained 1,2,4-benzenetriol, instead of ascorbic acid. The result was determined by visual inspection using the same criteria. The result is presented as Comparative Example 4.

As can be seen from the results shown in Table 5, the compounds that belong to the domain of the heterocyclic compound having a cyclic ester skeleton, a cyclic amide skeleton, or a cyclic imide skeleton were shown to be effective, confirming the effectiveness of the all heterocyclic compounds having the three kinds of skeletons specified by the present invention.

TABLE 5

| | Sodium nitrite amount (μmol/test) | Organic compound (1 μmol/test) | γ-CD amount (μmol/test) | Analyte | Determination (N = 5) | | | | |
|---|---|---|---|---|---|---|---|---|---|
| Ex. 11 | 50 | Hydantoin | 0.1 | Positive analyte | ++ | ++ | ++ | ++ | ++ |
| | | | | Negative analyte | − | − | − | − | − |
| Ex. 12 | 50 | Phthalimide | 0.1 | Positive analyte | +++ | ++ | ++ | +++ | +++ |
| | | | | Negative analyte | − | − | − | − | − |
| Ex. 13 | 50 | N,N'-Disuccinimidyl carbonate | 0.1 | Positive analyte | ++ | +++ | ++ | +++ | +++ |
| | | | | Negative analyte | − | − | − | − | − |

TABLE 5-continued

| | Sodium nitrite amount (μmol/test) | Organic compound (1 μmol/test) | γ-CD amount (μmol/test) | Analyte | Determination (N = 5) | | | | |
|---|---|---|---|---|---|---|---|---|---|
| Ex. 14 | 50 | 2-O-(α-D-Glucopyranosyl)-L-ascorbic acid | 0.1 | Positive analyte | ++ | ++ | ++ | +++ | +++ |
| | | | | Negative analyte | − | − | − | − | − |
| Ex. 15 | 50 | N-Acetylphthalimide | 0.1 | Positive analyte | +++ | ++ | ++ | ++ | ++ |
| | | | | Negative analyte | − | − | − | − | − |
| Ex. 16 | 50 | N-(tert-Butoxycarbonyloxy)-phthalimide | 0.1 | Positive analyte | +++ | +++ | ++ | +++ | ++ |
| | | | | Negative analyte | − | − | − | − | − |
| Ex. 17 | 50 | N-Acetoxysuccinimide | 0.1 | Positive analyte | ++ | +++ | ++ | ++ | ++ |
| | | | | Negative analyte | − | − | − | − | − |
| Ex. 18 | 50 | N-Carbobenzoxyoxy-succinimide | 0.1 | Positive analyte | ++ | ++ | ++ | ++ | ++ |
| | | | | Negative analyte | − | − | − | − | − |
| Ex. 19 | 50 | 2,3,7,8-Tetrahydroxy[1]-benzopyrrano[5,4,3-cde][1]benzo-pyran-5,10-dione dihydrate (ellagic acid dihydrate) | 0.1 | Positive analyte | ++ | ++ | +++ | +++ | ++ |
| | | | | Negative analyte | − | − | − | − | − |
| Com. Ex. 4 | 50 | 1,2,4-Benzenetriol | 0.1 | Positive analyte | ± | ± | ± | − | − |
| | | | | Negative analyte | ± | − | ± | − | − |

The effectiveness of the present invention can be demonstrated with ease when a compound having a cyclic imide skeleton with three nitrogen atoms, for example, the compound represented by [Chem. 5] is used as implemented in Example 11 because an effect similar to those shown in Table 5 also can be confirmed with this compound.

The usefulness of the present invention also can be demonstrated when any of the six-membered ring compounds having a cyclic imide skeleton with 1 to 4 nitrogen atoms represented by [Chem. 6] to [Chem. 9] is used as implemented in Example 11 because a nitrous acid also can be generated with the use of these compounds.

Specifically, the present inventors have found that the heterocyclic compound having at least one skeleton selected from the group consisting of a cyclic ester, a cyclic amide, and a cyclic imide functions in the same way in the generation of a nitrous acid.

Examples 20 to 25

The test conducted in Example 1 was repeated using the same procedure, except that the reagent retaining section [2] contained γ-cyclodextrin, instead of β-cyclodextrin, and that the reagent retaining section [3] contained N-acetoxysuccinimide, instead of ascorbic acid. The result was determined by visual inspection using the same criteria. The results are presented in Table 6.

TABLE 6

| | Sodium nitrite amount (μmol/test) | Organic compound amount (μmol/test) | γ-CD amount (μmol/test) | Analyte | Determination (N = 5) | | | | |
|---|---|---|---|---|---|---|---|---|---|
| Ex. 20 | 60 | 5 | 0.1 | Positive analyte | +++ | ++ | ++ | ++ | +++ |
| | | | | Negative analyte | − | − | − | − | − |
| Ex. 21 | 20 | 5 | 0.1 | Positive analyte | +++ | ++ | +++ | +++ | +++ |
| | | | | Negative analyte | − | − | − | − | − |
| Ex. 22 | 4 | 3 | 0.1 | Positive analyte | +++ | ++ | ++ | ++ | ++ |
| | | | | Negative analyte | − | − | − | − | − |
| Ex. 23 | 4 | 15 | 0.1 | Positive analyte | ++ | ++ | ++ | +++ | ++ |
| | | | | Negative analyte | − | − | − | − | − |

TABLE 6-continued

|  | Sodium nitrite amount (μmol/test) | Organic compound amount (μmol/test) | γ-CD amount (μmol/test) | Analyte | Determination (N = 5) | | | | |
|---|---|---|---|---|---|---|---|---|---|
| Ex. 24 | 20 | 15 | 0.1 | Positive analyte | +++ | +++ | +++ | +++ | +++ |
|  |  |  |  | Negative analyte | – | – | – | – | – |
| Ex. 25 | 50 | 30 | 0.1 | Positive analyte | +++ | +++ | +++ | +++ | +++ |
|  |  |  |  | Negative analyte | – | – | – | – | – |

Adenoviruses are known to cause infections with symptoms similar to the symptoms seen in *streptococcus* infections. An immunochromatographic kit capable of simultaneously testing both *streptococcus* and adenovirus (Adv) using the ascorbic acid system is produced in the manner described below.

The determining section is fabricated on the chromatographic medium [1] in the same manner as in Example 1, except that, instead of applying the rabbit-derived anti-*streptococcus* monoclonal antibodies (first antibody), a plurality of determination sections was provided by applying mouse-derived anti-adenovirus monoclonal antibodies (first antibody) at a position parallel to the determination section fabricated by applying rabbit-derived anti-*streptococcus* monoclonal antibodies (first antibody), using the technique used in Example 1.

The label substance solution is produced in the same manner as in Example 1, except that a mixture of mouse-derived anti-*streptococcus* polyclonal antibodies (second antibody) and rabbit-derived anti-adenovirus polyclonal antibodies (second antibody) was used instead of the rabbit-derived anti-*streptococcus* polyclonal antibodies (second antibody), using the technique used in Example 1.

The reagent retaining section [2], the reagent retaining section [3], the immunochromatography test piece, and the analyte diluting solution are also produced in the same manner as in Example 1.

With the immunochromatography test piece and the analyte diluting solution produced above, an experimental immunochromatographic kit capable of simultaneously testing both *streptococcus* and adenovirus (Adv) was produced experimentally by impregnating the sample pad (reagent retaining section [2]) and the conjugate pad (reagent retaining section [3]) with sodium nitrite and ascorbic acid, respectively. The kit was used to test a negative analyte (extractant), and a positive analyte, for which *streptococcus* inactivated antigens ($2 \times 10^6$ org/mL) and adenovirus inactivated antigens (1 ng/mL) were used. The samples were evaluated by visually checking the test lines after 5 minutes from dropping the analytes. The results are presented in Table 7.

TABLE 7

|  | Test line for *streptococcus* | Test line for Adv |
|---|---|---|
| Extractant | – | – |
| *streptococcus* inactivated antigen ($2 \times 10^6$ org/mL) | ++ | – |
| Adv inactivated antigen (1 ng/mL) | – | +++ |

As clearly indicated by the results shown in Table 7, a thicker test line was observed for adenovirus than for *streptococcus* in the tests conducted with ascorbic acid for the negative analyte (extractant), and for the positive analyte using *streptococcus* inactivated antigens ($2 \times 10^6$ org/mL) and adenovirus inactivated antigens (1 ng/mL).

When carrying out a *streptococcus* test using the immunochromatography method of the present invention, sodium nitrite should be used in an amount of preferably 10 to 100 μmol per test, and ascorbic acid and N-hydroxysuccinic acid should be used in an amount of preferably 0.1 to 100 μmol, more preferably 0.1 to 50 μmol, further preferably 0.1 to 30 μmol, optimally 1 to 15 μmol per test. When adding a cyclic oligosaccharide, it should be used in an amount of preferably 0.02 to 0.5 μmol per measurement (kit). This is highly effective because the test, when conducted with these ranges, enables accurate determination with a high development rate and a high S/N ratio, without causing precipitation of the protein component, or aggregation of antibody-immobilized metal particles.

While there has been described a certain embodiment of the invention in detail, it will be understood by a skilled person that various changes and modifications may be made thereto without departing from the spirit and scope of the invention. This patent application is based on Japanese patent application (No. 2015-141968) filed Jul. 16, 2015, the entire contents of which are hereby incorporated by reference.

INDUSTRIAL APPLICABILITY

The present invention is highly advantageous in that it enables testing of respiratory infection-causing gram-positive bacteria, particularly group A β hemolytic streptococci, or simultaneous testing of gram-positive bacteria and adenoviruses in a quick, easy, and proper fashion. The invention enables a clinical test to be conduced with high sensitivity, both quickly and properly, not only in hospitals and clinics but by individuals with no special skills. The invention has potential use for early diagnosis of infected patients, and for providing an appropriate treatment.

Further, because the invention does not require the laborious process of preparing the unstable nitrous acid for every test by reacting a nitrite salt with an acidic solution, the invention improves test efficiency, and reduces labor, in addition to improving the handling, efficiency, and accuracy of the immunochromatographic kit of the present invention. This highly contributes to the development of test industries, and medical industries.

REFERENCE SIGNS LIST

1: Chromatographic medium [1]
2: Sample dropping section [2] (reagent retaining section [2])
3: Antigen extracting section [3] (reagent retaining section [3])
4: Label-substance retaining section [4]
5. Absorbing section [5]
6. Analyte processing solution (extractant) [6]

The invention claimed is:

1. An immunoassay method that uses a test device, the method comprising:
extracting an antigen of a detection target in an analyte with an extraction agent; and
detecting the antigen with a detection reagent capable of specifically binding the antigen,
wherein the extraction agent is a nitrous acid generated on the test device by a contact reaction between a nitrite salt and a heterocyclic compound having at least one skeleton selected from the group consisting of a five- or six-membered ring cyclic ester, a five- or six-membered ring cyclic amide, and a five- or six-membered ring cyclic imide;
wherein the detection target comprises a gram-positive bacterium;
wherein the antigen is a group-specific polysaccharide present in the cell wall of the gram-positive bacterium; and
wherein an assay is conducted in the presence of a cyclic oligosaccharide.

2. The immunoassay method according to claim 1, wherein the heterocyclic compound having the cyclic ester skeleton is a five-membered ring compound having 1 to 2 oxygen atoms.

3. The immunoassay method according to claim 1, wherein the heterocyclic compound having the cyclic amide skeleton, and the heterocyclic compound having the cyclic imide skeleton are five- or six-membered ring compounds having 1 to 3 nitrogen atoms.

4. The immunoassay method according to claim 1, wherein the heterocyclic compound having at least one skeleton selected from the group consisting of a five- or six-membered ring cyclic ester, a five- or six-membered ring cyclic amide, and a five- or six-membered ring cyclic imide is used in an amount of 0.1 to 100 μmol per measurement.

5. The immunoassay method according to claim 1, wherein the detection reagent is an antibody derived from at least one animal species selected from rabbit, goat, and mouse.

6. The immunoassay method according to claim 1, wherein the detection target further comprises an adenovirus.

7. The immunoassay method according to claim 1, wherein the gram-positive bacterium is a hemolytic *streptococcus*.

8. An immunochromatographic kit for detecting an antigen of a detection target in an analyte with a detection reagent capable of binding the antigen,
the immunochromatographic kit comprising:
a detection reagent;
an analyte diluting solution; and
an immunochromatographic device;
wherein the immunochromatographic device includes:
a sample dropping section;
an antigen extracting section;
a label-substance retaining section;
a chromatographic medium having a detection section; and
an absorbing section;
wherein the analyte diluting solution and the sample dropping section contains a nitrite salt;
wherein the antigen extracting section contains a heterocyclic compound having at least one skeleton selected from the group consisting of a five- or six-membered ring cyclic ester, a five- or six-membered ring cyclic amide, and a five- or six-membered ring cyclic imide;
wherein the detection target comprises a gram-positive bacterium;
wherein the antigen is a group-specific polysaccharide present in the cell wall of the gram-positive bacterium;
wherein the detection reagent is capable of specifically binding said antigen; and
wherein the kit contains a cyclic oligosaccharide.

9. The immunochromatographic kit according to claim 8, wherein the heterocyclic compound having at least one skeleton selected from the group consisting of a five- or six-membered ring cyclic ester, a five- or six-membered ring cyclic amide, and a five- or six-membered ring cyclic imide is contained in an amount of 0.1 to 100 μmol per kit.

10. The immunochromatographic kit according to claim 8, wherein the detection reagent is an antibody derived from at least one animal species selected from rabbit, goat, and mouse.

11. The immunochromatographic kit according to claim 8, wherein at least one of the analyte diluting solution and the sample dropping section contains a cyclic oligosaccharide.

12. The immunochromatographic kit according to claim 8, wherein the detection target further comprises an adenovirus.

13. The immunochromatographic kit according to claim 8, wherein the gram-positive bacterium is a hemolytic *streptococcus*.

14. The immunochromatographic kit according to claim 8, wherein the label-substance retaining section includes a metal nanoparticle.

* * * * *